US011257567B2

(12) United States Patent
Markovic et al.

(10) Patent No.: US 11,257,567 B2
(45) Date of Patent: Feb. 22, 2022

(54) MODELING OF SYSTEMATIC IMMUNITY IN PATIENTS

(71) Applicants: Mayo Foundation for Medical Education and Research, Rochester, MN (US); James D. Turner, College Station, TX (US); Harold P. Frisch, Grinnell, IA (US)

(72) Inventors: Svetomir N. Markovic, Rochester, MN (US); James D. Turner, College Station, TX (US); Harold P. Frisch, Grinnell, IA (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 844 days.

(21) Appl. No.: 15/778,453

(22) PCT Filed: Nov. 23, 2016

(86) PCT No.: PCT/US2016/063602
§ 371 (c)(1),
(2) Date: May 23, 2018

(87) PCT Pub. No.: WO2017/091727
PCT Pub. Date: Jun. 1, 2017

(65) Prior Publication Data
US 2018/0357359 A1 Dec. 13, 2018

Related U.S. Application Data

(60) Provisional application No. 62/258,897, filed on Nov. 23, 2015.

(51) Int. Cl.
*G16B 5/30* (2019.01)
*G16B 5/00* (2019.01)
(Continued)

(52) U.S. Cl.
CPC ........... *G16B 5/30* (2019.02); *G16B 5/00* (2019.02); *G16B 40/00* (2019.02); *G16B 40/10* (2019.02); *G16H 50/20* (2018.01); *G16H 50/50* (2018.01)

(58) Field of Classification Search
None
See application file for complete search history.

(56) References Cited

U.S. PATENT DOCUMENTS

| 2009/0104596 A1 | 4/2009 | Assadi-Porter et al. |
| 2014/0025358 A1* | 1/2014 | Hill .................. G16B 5/00 703/2 |

(Continued)

OTHER PUBLICATIONS

Byrne, "Dissecting cancer through mathematics: from the cell to the animal model," Nat. Rev. Cancer, 10(3):221-30, Mar. 2010.
(Continued)

*Primary Examiner* — William C Trapanese
(74) *Attorney, Agent, or Firm* — Fish & Richardson P.C.

(57) ABSTRACT

In one implementation, a computer-implemented method includes accessing patient-derived blood data; identifying biomarker pair interactions based on signal processing of the patient-derived blood data; generating a data model that characterizes one or more aspects of human immune system interactions based on reverse engineering of the human immune system interactions using the identified biomarker pair interactions; evaluating suitability of the data model, wherein the evaluating includes: statistically testing the data model in characterizing correlations between biomarker pairs; decomposing the data model to determine (i) model order accuracy, (ii) whether biomarker nodes act in together or opposite each other, and (iii) normalized data with dynamic effects of homeostasis removed; and quantifying degrees to which the data model accurately correlates patient (Continued)

treatments to patient outcomes; and providing the data model for use in treatment-based decision making based on the evaluating.

15 Claims, 24 Drawing Sheets

(51) Int. Cl.
 *G16B 40/00* (2019.01)
 *G16H 50/50* (2018.01)
 *G16B 40/10* (2019.01)
 *G16H 50/20* (2018.01)

(56) References Cited

U.S. PATENT DOCUMENTS

2015/0018238 A1 1/2015 Wong et al.
2015/0038376 A1 2/2015 Tian et al.

OTHER PUBLICATIONS

Caravagna et al., "Tumour suppression by immune system through stochastic oscillations," J. Theor. Biol., 265(3):336-45, Aug. 2010.
De Boer et al., "Turnover rates of B cells, T cells, and NK cells in simian immunodeficiency virus-infected and uninfected rhesus macaques," J. Immunol., 170(5):2479-87, Mar. 2003.
De Pillis et al., "Chemotherapy for tumors: an analysis of the dynamics and a study of quadratic and linear optimal controls," Math Biosci., 209(1):292-315, Sep. 2007.
De Pillis et al., "Mathematical model creation for cancer chemo-immunotherapy," Computational and Mathematical Methods in Medicine, 10(3):165-84, Sep. 2009.
De Pillis et al., "Mixed immunotherapy and chemotherapy of tumors: modeling, applications and biological interpretations," J. Theor. Biol., 238(4):841-62, Feb. 2006.
De Pillis LG, Radunskaya AE, Wiseman CL. A validated mathematical model of cell-mediated immune response to tumor growth. Cancer Res., 65(17):7950-8, Sep. 2005.
Diefenbach et al., "Rae1 and H60 ligands of the NKG2D receptor stimulate tumour immunity," Nature, 413:165-71, Sep. 2001.
D'Onofrio, "Spatiotemporal effects of a possible chemorepulsion of tumor cells by immune system effectors," J. Theor. Biol., 296:41-8, May 2012.
Eftimie et al., "Modeling anti-tumor Th1 and Th2 immunity in the rejection of melanoma Selective expansion and partial activation of human NK cells and NK receptor-positive T cells by IL-2 and IL-15," J. Theor. Biol., 265(3):467-80, Aug. 2010.
Hellerstein et al., "Directly measured kinetics of circulating T lymphocytes in normal and HIV-1-infected humans," Nat. Med., 5:83-9, Jan. 1999.
International Search Report in International Application No. PCT/US2016/063602 dated Feb. 2, 2017, 2 pages.
Kirschner and Panetta, "Modeling immunotherapy of the tumor-immune interaction," J. Math Biol., 37:235-52, Sep. 1998.
Kuznetsov et al., "Nonlinear dynamics of immunogenic tumors: parameter estimation and global bifurcation analysis," Bull Math Biol., 56:295-321, Mar. 1994.
Mallet et al., "A cellular automata model of tumor-immune system interactions," Theor. Biol., 239:334-50, Apr. 2006.
Meropol et al., "Evaluation of natural killer cell expansion and activation in vivo with daily subcutaneous low-dose interleukin-2 plus periodic intermediate-dose pulsing," Cancer Immunol. Immunother., 46:318-26, Aug. 1998.
Patel et al., "A cellular automaton model of early tumor growth and invasion," J. Theor. Biol., 213(3):315-31, Dec. 2001.
Wheldon et al., "Optimal radiotherapy of tumour cells following exponential-quadratic survival curves and exponential repopulation kinetics," Br. J. Radiol., 50:681-2, Sep. 1977.

\* cited by examiner

| Cytokine | Cancerfree | Cancer | CF-C | Strength |
|---|---|---|---|---|
| VEGF | 0.44886 | 0.14444 | 30.441 | strong |
| Fractalkine | 0.37385 | 0.08854 | 28.531 | strong |
| MCP-3 | 0.24564 | 0.07070 | 17.494 | strong |
| TNFb | 0.16383 | 0.04475 | 11.908 | strong |
| IL-1ra | 0.15053 | 0.08983 | 6.070 | significant |
| IL-12p40 | 0.09161 | 0.06575 | 2.587 | significant |
| IFNg | 0.05063 | 0.02639 | 2.424 | significant |
| IFNa2 | 0.08924 | 0.06752 | 2.172 | significant |
| MCP-1 | 0.69618 | 0.68110 | 1.509 | significant |
| IL-5 | 0.01234 | 0.00197 | 1.038 | significant |
| IL-12p70 | 0.02010 | 0.01535 | 0.475 | weak |
| IL-7 | 0.00970 | 0.00528 | 0.442 | weak |
| IL-10 | 0.02138 | 0.01904 | 0.235 | weak |
| IL-9 | 0.00536 | 0.00371 | 0.166 | weak |
| MIP-1a | 0.02680 | 0.02521 | 0.158 | weak |
| IL-6 | 0.00997 | 0.00922 | 0.075 | weak |
| IL-1b | 0.00749 | 0.00770 | -0.021 | weak |
| IL-2 | 0.00581 | 0.00678 | -0.097 | weak |
| TNFa | 0.01488 | 0.02588 | -1.100 | significant |
| MIP-1b | 0.06090 | 0.07415 | -1.326 | significant |
| IL-4 | 0.00871 | 0.02315 | -1.445 | significant |
| GM-CSF | 0.01713 | 0.03741 | -2.028 | significant |
| IP-10 | 0.83223 | 0.91214 | -7.991 | significant |
| IL-8 | 0.04661 | 0.17811 | -13.150 | strong |

FIG. 16

MODELING OF SYSTEMATIC IMMUNITY IN PATIENTS

CROSS-REFERENCE TO RELATED APPLICATIONS

This application is a National Stage application under 35 U.S.C. § 371 of International Application No. PCT/US2016/063602, having an International Filing Date of Nov. 23, 2016, which claims priority to U.S. Application Ser. No. 62/258,897, filed on Nov. 23, 2015. The disclosure of the prior applications is considered part of the disclosure of this application, and is incorporated in its entirety into this application.

TECHNICAL FIELD

This document generally describes computer-based technology for modeling systematic immunity in patients with metastatic melanoma, for example, using clinical data.

BACKGROUND

The treatment of cancer using modulation of host immunity (cancer immunotherapy) is an old concept that has recently generated renewed enthusiasm as novel agents targeting elements of the systemic immune system in patients (blocking antibodies to checkpoint inhibitors, CTLA4 and/or PD1) have been found to yield favorable clinical results. Unlike previously studied recombinant cytokines (interferons, interleukin-2), current immune checkpoint blocking antibodies (ipilimumab, pembrolizumab, nivolumab) appear to achieve their therapeutic effects by interfering with tumor-derived inhibition of T cell function. While clinical results are still modest relative to pre-clinical success, the therapeutic benefits have been found to be sufficient to stimulate a massive effort in combination treatments involving these agents. Efforts to improve upon early clinical successes have focused on drug combinations. Such clinical efforts have been largely empiric, driven primarily by clinical observations, rationalization of potential combinatorial benefit based on postulated (pre-clinical) mechanisms of action, and minimization of cumulative toxicity.

SUMMARY

In one implementation, a computer-implemented method includes accessing, by a computer system, patient-derived blood data; identifying, by the computer system, biomarker pair interactions based on signal processing of the patient-derived blood data; generating, by the computer system, a data model that characterizes one or more aspects of human immune system interactions based on reverse engineering of the human immune system interactions using the identified biomarker pair interactions; evaluating, by the computer system, suitability of the data model to be used in treatment-based decision making, wherein the evaluating includes: statistically testing, by the computer system, the accuracy of the data model in characterizing correlations between biomarker pairs; decomposing, by the computer system, the data model to determine (i) model order accuracy, (ii) whether biomarker nodes act in together or opposite each other, and (iii) normalized data with dynamic effects of homeostasis removed; and quantifying, by the computer system, degrees to which the data model accurately correlates patient treatments to patient outcomes using one or more sets of known patient treatments and outcomes; and providing, by the computer system, the data model for use in treatment-based decision making based on the evaluating.

In another implementation, a computer system includes a data storage device storing patient-derived blood data; one or more computing devices that each include one or more processors and memory storing instructions, wherein the instructions, when executed, cause the one or more processors to perform operations including: accessing the patient-derived blood data from the data storage device; identifying biomarker pair interactions based on signal processing of the patient-derived blood data; generating a data model that characterizes one or more aspects of human immune system interactions based on reverse engineering of the human immune system interactions using the identified biomarker pair interactions; evaluating suitability of the data model to be used in treatment-based decision making, wherein the evaluating includes statistically testing the accuracy of the data model in characterizing correlations between biomarker pairs; decomposing the data model to determine (i) model order accuracy, (ii) whether biomarker nodes act in together or opposite each other, and (iii) normalized data with dynamic effects of homeostasis removed; and quantifying degrees to which the data model accurately correlates patient treatments to patient outcomes using one or more sets of known patient treatments and outcomes; and providing the data model for use in treatment-based decision making based on the evaluating.

In another implementation, a non-transitory computer readable medium storing instructions that, when executed by one or more computing devices, cause the one or more computing devices to perform operations includes accessing patient-derived blood data; identifying biomarker pair interactions based on signal processing of the patient-derived blood data; generating a data model that characterizes one or more aspects of human immune system interactions based on reverse engineering of the human immune system interactions using the identified biomarker pair interactions; evaluating suitability of the data model to be used in treatment-based decision making, wherein the evaluating includes: statistically testing the accuracy of the data model in characterizing correlations between biomarker pairs; decomposing the data model to determine (i) model order accuracy, (ii) whether biomarker nodes act in together or opposite each other, and (iii) normalized data with dynamic effects of homeostasis removed; and quantifying degrees to which the data model accurately correlates patient treatments to patient outcomes using one or more sets of known patient treatments and outcomes; and providing the data model for use in treatment-based decision making based on the evaluating.

Such implementations can optionally include one or more of the following features. The data model can include a Kolmogorov-Gabor polynomial knowledge constraint model. The data model can be generated using one or more predator-prey equations. The data model can be generated further using one or more reverse engineering techniques that cause the data model to correlate natural modes of system behavior. The data model can be generated to model biomarker cause and effect dynamic integration networks.

The details of one or more embodiments are set forth in the accompanying drawings and the description below. Other features and advantages will be apparent from the description and drawings, and from the claims.

DESCRIPTION OF DRAWINGS

FIG. 16 depicts example cancer free vs. cancer patient average cytokine biomarker profiling measures.

Like reference symbols in the various drawings indicate like elements.

DETAILED DESCRIPTION

Figure 1:
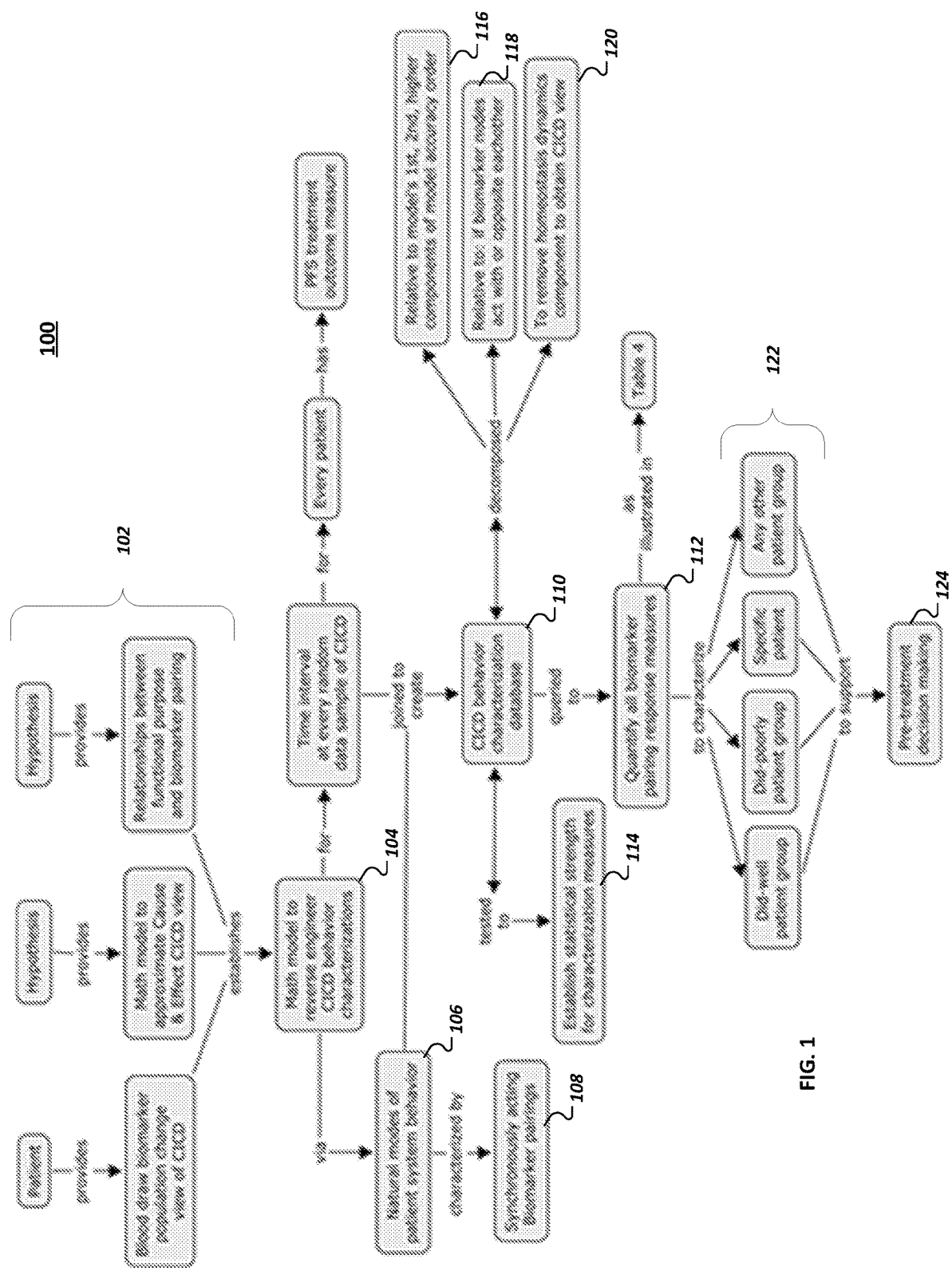
FIG. 1 is a flowchart of an example data modeling technique that provides an analysis process framework.

Clinical advances in cancer immuno-therapeutics underscore a need for improved understanding of the complex relationship between cancer and the multiple, multi-functional, inter-dependent, cellular and humoral mediators/regulators (biomarkers) of the human immune system. This is best illustrated in the setting of anti-CTLA4 and anti-PD1 therapy in patients with metastatic melanoma. Both agents act on elements of the patient's immune system and yield survival advantages in a number of patients with advanced melanoma. However, unlike preclinical results, overall clinical success remains modest therapeutic side effects are significant (some are life-threatening), and the financial burden to patients can be substantial. A better understanding of the underlining biology of the human cancer/immune interactions may lead not only to improvements in the efficacy of existing immune therapies (patient selection; drug combinations) but also lend insight into new therapeutic targets that may ultimately yield dramatic advances in long term therapeutic efficacy.

This document describes computer-based technology for modeling and quantitatively assessing clinical outcomes based on pre-treatment and treatment induced changes in systemic immunity that can lead to positive and/or negative outcomes. Human systems can be modeled in ways that incorporate a multitude of cancer/immune interactions assessed in patients with cancer, yielding insights into critical points of immune regulation with significant potential of impacting clinical outcomes. A variety of different modeling techniques can be used, such as aerospace engineering signal processing algorithms to analyze the state of system immunity in cancer patients based on dynamic characterizations of a set of serially obtained peripheral blood biomarkers. For example, hypothesized sets of model equations for observable systemic behaviors of biomarker populations can be formulated and solved as part of the modeling. In another example, advanced signal processing and data mining tools can be used to identify and quantify underlying interactions, cross coupling relationships strengths, and associated immune-control pathways accessible to clinical intervention.

For example, biomarker interactions can be modeled by matrix generalizations of non-linear predator-prey equations commonly used to model biological system dynamics. To model biomarker value transition between sample points, linear interpolation can be used, for example. This can be used to reverse engineer a time record of biomarker population driving action. Any of a variety of modeling techniques and structures, such as Kolmogorov-Gabor polynomial, can be used to model biomarker population driving actions. Such modeling can exploit biological knowledge regarding polynomial elements to define whether the element is biologically possible or impossible. First and second order interaction models can be assembled for analysis and concepts from linear second order differential systems; modal analysis and operational calculus can underpin operational processes. Matrix models can link biomarker output. Such matrices, dependent upon models employed and serially collected biomarker data, can enable a computer system to identify and quantify underlying interactions, cross coupling relationship strengths, and associated immune-control pathways accessible to clinical intervention potential. Per patient consistency of results across their respective test periods and across all patients have been shown using such techniques and systems. Results show (expected) patient variability overlaying a significant cross patient commonality. Such techniques and systems have been developed to extract and quantify biologically meaningful insights into the human cancer/immune interface, for example. By viewing results across patients, clinical treatment outcome sensitive biomarker pairings can be identified, as well as clinical intervention biomarker access points. Identified biomarker pairings and their quantified relationships to immunology knowledge can provide powerful anti-tumor immune response insight.

In another example, several specific biomarkers associated with the cytokine modulation of immune system cells and resultant system behavior have been identified. Such models have been used to demonstrate capabilities for identifying interacting biomarkers pairs, which are shown to highly correlate with known interactions. For instance, with melanoma cancer such techniques and systems have been used to identify IP-10 and MCP-1 as the dominant biomarkers for describing cell action modulation and system behavior. These model-based predictions have been independently validated experimentally. The power of these techniques and systems is in its ability to extract global information, rather than through exhaustive highly targeted clinical investigations. Such capabilities can additionally be extended, for example, to provide broad-based tools for addressing metastatic melanoma in patient specific situations and in human immune system interactions in general.

Predictions generated from data modeling techniques can be cross validated with known interactions, such as those obtained by working with biological subject matter experts. Proof-of-concept explorations of data model-based analysis capabilities and built in extensibility pathways for the inclusion of increasing degrees of modeling fidelity with methods for extracting biologically meaningful insights for guiding therapeutic interventions for improving patient outcomes with metastatic melanoma can be performed.

Experimentation using such data modeling techniques have been performed. For example, first order analysis numerical experiments have been performed and demonstrated that the described data modeling techniques are able to identify anti-tumor immune response insight with respect to clinical treatment outcome sensitive biomarker pairings existing across patients, as well as quantifying their effectivity relationships and clinical intervention access points. These results provide evidence that signal based systems analysis modeling of patient derived data can lead to patient specific clinical insights as they pertain to the biology of disease (antitumor immunity) in humans. Techniques for generating data models can be based on classical predator-prey analysis paradigm and can be structured to support multi-dimensional predator-prey interaction studies. Such an analysis framework can be designed to accommodate the sequential inclusion of analysis modeling detail at increasingly deep orders of modeling fidelity, which can provide a quantitative basis for understanding immune system pathways that exhibit the highest degrees of accessible effectivity. Such techniques and resulting data models can have any of a variety of possible applications, such as addressing metastatic melanoma in particular and human immune system interactions in general.

In recent years, efforts by multiple groups have brought new insights into the state of the systemic immunity in patients with cancer. A number of findings suggest a constellation of multiple abnormalities in systemic immunity of cancer patients that have the potential to directly impact not only the clinical response to immune therapy but also the natural history of the malignant disease. The panoply of multiple aberrancies in the immune system of cancer patients may represent a manifestation of a complex set of biological processes that can benefit from an interrogative approach capable of complex systems analyses taking into account multiple variably interdependent parameters (biomarkers), such as the data modeling and analysis techniques described in this document, which provide a computer-based interrogative approach that reverse engineers models of the human immune system in patients with metastatic melanoma utilizing, for example, peripheral blood derived measurements (time-series) of immune function (biomarkers). Such a data-driven approach can be implemented with engineering analysis techniques used to investigate anomalous, performance impacting, electro-mechanical system behaviors.

Reverse engineering behavior models can capture structural representational features, such as an ill-defined collection of system disturbances, an ill-defined environment, an ill-defined connection network of biomarker feedback relationships, modularity, adaptability, robustness, redundancy, and/or other features. Dynamic characterizations for uncovering networks of interacting biomarkers can be derived from patient blood sample (immune biomarker) data via model based characterizations of the systemic behavior model's structure. Coupling effects present in the immune systems environment can be accounted for in biomarker interaction studies and the computer-based data modeling provide a test platform (e.g., virtual reality test platform) for exploring the action-reaction consequences of specific clinical treatment options. This can be achieved, for example, by solving inverse problems that use observed response data to quantify hypothesized systemic behavior models rich in insight creation potential.

Although standard engineering approaches to complex system analysis suggest beginning with assumptions of a linear polynomial behavior representational state space model, evaluation of biology modeling suggests that data modeling should begin with nonlinear models. Accordingly, data modeling can be performed using nonlinear polynomial representation, which have been found to yield numerical results accurate to order ~4 (cubic, tri-linear) numerical accuracy.

The disclosed techniques for data model generation provide the ability to capture near-periodic behaviors between interacting populations and that by a simple non-traditional matrix collection of polynomial's terms, access to traditional state space linear system theory methods can be enabled. This can not only map non-linear computational problems to a summation of traditional linear state space matrix computation problems; but it can also provide resultant behavior decompositions that have detail interaction biology meaning and embedded insights. Since data models can represent the actual immune system behaviors from observations, nonlinear coupling interactions can become observable, which can result from the lack of analyst imposed simplifications that may otherwise impact the data extraction process.

Data modeling techniques can be comprehensive so as to provide an order ~3 accuracy via the patient biomarker data used to quantify modeling approximants. Data mining decision-making capabilities can be performed using any of a variety of techniques, such as Singular Value Decomposition (SVD) techniques. Generalized predator-prey paradigms, such as those for system dynamics, can modes patient pre-treatment states in the immune system. Coupled subsystems can emerge as synchronously acting biomarker pairing relationships within observation time instance characterizations and over the full blood draw test period, which can create both time instant detail and resultant test period duration based analysis views. Databases of these behavior characterizations can then be used for patient database querying and treatment decision-making. Leveraging SVD-based computational decompositions with observed biology, as well as immunology behavioral response expectations, can lead to empirical insights. Abductive inference insights can be gleaned by investigating analogies with observed behaviors seen in electromechanical linear harmonic systems. Proof-of-concept methodology demonstration can illustrate the discovery that pre-treatment occurrence frequency of specific data modeled observable biomarker pairings bias patient clinical outcome. Additional results can expose associated root cause insights and identify research pathways to deeper immune regulatory understanding and clinical treatment potential.

Brief Overview of Data Modeling and Analysis

FIG. 1 is a flowchart of an example data modeling technique 100 that provides an analysis process framework. The example technique 100 includes data flow linkages from data collections and model creation steps used for data processing, to the dynamics characterization database creation and data mining steps. The example technique 100 can be performed by any of a variety of appropriate computer systems, such as a system including one or more computing devices (e.g., server, client computing device, desktop computer, laptop, mobile computing device). For example, the technique 100 can be performed by a computer server system with one or more computer servers that are programmed to execute the technique 100, such as a distributed server system (e.g., cloud-based computer system). Such an example computer system for performing the technique 100 is named Cancer Immune Control Dynamics (CICD), and is described in this document to illustrate the disclosed computer-based technology. Computer systems and/or computing devices other than the CICD can also be used to implement and/or perform the technique 100 and other aspects of the computer-based technology described throughout this document.

The technique 100 can include analyst/user identified patient-derived blood products, such as through data processing tools for collecting the patient-derived blood data; applying advanced signal processing for extracting biomarker pair interactions; and network coupling information (102). After collecting the patient data, CICD (example computer system) computes insight rich reverse engineering characterization views of immune system interactions (104).

The computational analysis activity can be split into two parts. First, the generalized predator prey model can be decomposed using singular value decomposition techniques to identify natural modes of behavior associated with 1st (linear), 2nd(bilinear), . . . higher order accuracy views (106). This analysis step can extract information regarding the coupled nature of biomarker pairs that move synchronously in each natural mode of behavior in response to external inputs (108). Biomarker pairing data can be collected and stored in CICD's behavior database (110). Specific biomarker pairs can be identifies, ranked, and targeted for exploring intervention strategies. With this reverse engineering model data available, the remainder of CICD's processing can be concerned with "data mining" activities. Statistical tests can be performed on each biomarker pair to establish the value of the data (114). Next the behavior database is further processed to establish: the accuracy of the decomposed data for linear, bilinear, . . . higher order accuracy interactions (116); identify if biomarker pairing nodes move in the same or opposite directions (118); and normalize the data for biomarker pairing response outcome biasing investigations enabled by removing the dynamics effects of homeostasis (120). The next level of processing examines each biomarker pair to quantify the degree to which CICD analysis inferred response correlates with patient treatment outcome (112); that is: did the patient do well, did the patient do poorly; establish insights for specific patients; and investigate relationships between patient outcome groups (122). Overall, the strategy is to extract patterns in the data that provide useful insights for intervention strategies. Lastly the clinician uses the derived data for designing patient specific intervention approaches (124).

Materials and Techniques

Patient Population

Studies were performed using a subset of available laboratory and clinical data from a previously completed clinical trial in adult patients with the diagnosis of metastatic melanoma. Eligible patients exhibited a good ECOG performance status (ECOG 0, 1 or 2). All patients agreed to provide sequential daily blood specimens (at least 10 over the course of 14 consecutive days). All peripheral blood samples (collected in Na-heparin Vacutainer tubes) were collected while fasting, between 8 and 10 AM (avoiding circadian variation). Samples were immediately processed and frozen for later batch analysis.

CICD Patient Data Records Linear Interpolation

Figure 2:
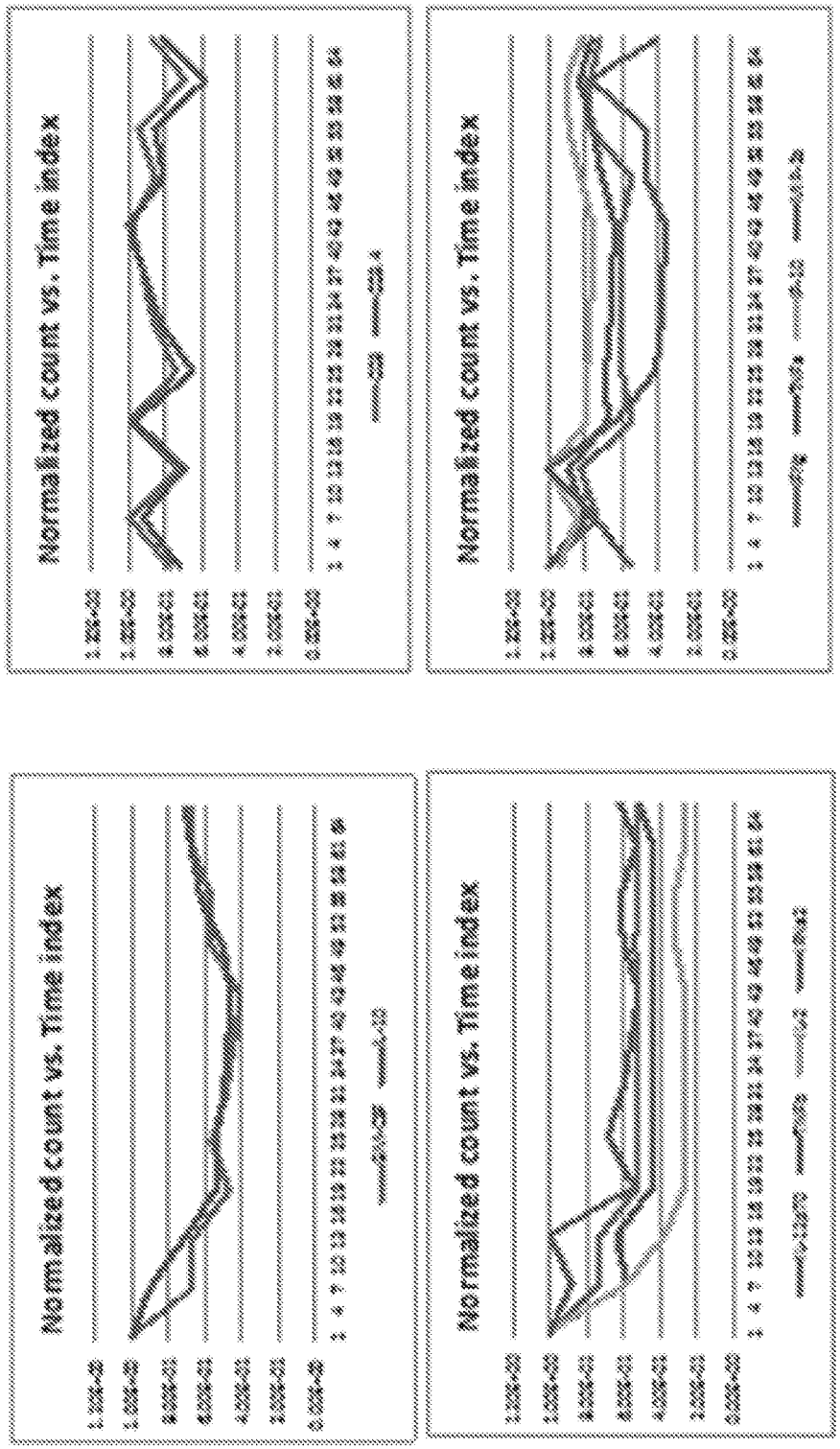
FIG. 2 depicts example graphs for 12 of 31 biomarker measurements vs. 10 blood draw sample times for a typical patient data record.

Computational data modeling techniques can operate satisfactorily with sparse information; however, analysts may be challenged to draw valid inferences from overly sparse representations. To this end, it can be a goal of a system to establish a balance between the computational demands of too much CICD data and the challenges of too little data. To illustrate this, FIG. 2 depicts example graphs for 12 of 31 biomarker measurements vs. 10 blood draw sample times for a typical patient data record. The vertical scale reflects biomarker data normalized to have max value equal 1.0, so that rhythms and synchronicities can be more clearly detected and compared. Per graph biomarker selection sets are chosen to highlight similar patterns of non-harmonic rhythmic response and synchronicity typically observed across all patients. Non-linear CICD analysis can use unscaled linearly interpolated data records. Linear interpolation can be used to connect biomarker measures across data sampling time gaps and increase the number of test period data points. Data interpolated records can contain 6 equally spaced time steps per day for the full 12-day blood sample collection period. Linear interpolation can be used because it does not introduce extraneous dynamics and it preserves all data measurement ratios between blood draw sample instances. This approach may be adopted because it is well accepted by dynamics analysis specialists that analysis anomalies can occur when polynomial based curve-fitting methods, created to manipulate data for visualization purposes, are applied within a reverse engineering dynamics analysis process. Algorithmically, the problems may arise because a "smoothed" data record introduces physically unrealizable dynamics into a coarsely measured response curve to obtain a visually satisfying continuous time response view. Access to more frequently observed data may increase data quality and minimize the need for linear interpolation. When finite difference cause and effect relationships and time sequenced observed data begin to align, the use of interpolation may end.

To embed a tumor size dependent parameter into CICD analysis for future sensitivity studies, patient data records can also include a tumor size measure, as estimated per patient by the RECIST (Response Evaluation Criteria in Solid Tumors) criteria. CICD analysis can assume that no substantive change in tumor size occurs during the 12-day test period. To relate this linear tumor measure to the volumetric based measures of biomarker populations, RECIST values can be raised to the 2.25 power. This power law can map linear diameter tumor size measures to a value range that spans cross patient volumetric biomarker population size mean values. To date, significant behavior sensitivities to the tumor size parameter have not been detected.

CICD Matrix Equations Viewed as a Generalized Predator-Prey Problem

Before presenting the multivariable CICD modeling techniques used for signal processing, it can be helpful to gain insight by reviewing the classical 2-variable Lotka-Volterra equations, also known as the predator-prey equations. Examples of these are shown in Equations 1 as follows:

$$\frac{dX}{dt} = aX + bXY \quad (1)$$
$$\frac{dY}{dt} = cY + dXY$$

To illustrate CICD's matrix equation format, these equations can be re-expressed as:

$$\left\{ \begin{array}{c} \frac{dX}{dt} \\ \frac{dY}{dt} \end{array} \right\} = \begin{bmatrix} X & 0 \\ 0 & Y \end{bmatrix} \left\{ \begin{array}{c} a \\ c \end{array} \right\} + \begin{bmatrix} XY & 0 \\ 0 & XY \end{bmatrix} \left\{ \begin{array}{c} b \\ d \end{array} \right\} \quad (2)$$

or $$\left\{ \begin{array}{c} \frac{dX}{dt} \\ \frac{dY}{dt} \end{array} \right\} = K_U \left\{ \begin{array}{c} a \\ c \end{array} \right\} + K_B \left\{ \begin{array}{c} b \\ d \end{array} \right\}$$

In Equation 2, CICD's characterization matrices $K_U$, $K_B$ are the uni- and bi-linear function matrices of predator X and prey Y state variables while (a, b, c, d) can be the unknown predator-prey system specification parameters. For CICD reverse engineering analysis it can be the variables of state that are known and it can be the patient population change causing parameters that are the unknowns. By analogy, CICD analyzes an observed multi-variable predator-prey problem where the observed rhythmic responses of bio-marker data records can be the variables used to characterize CICD predator-prey state. This model is useful for two reasons: (1) an equilibrium solution can be found, which defines a prey growth representation that is balanced with predation harvesting of prey, and (2) the quadratic nature of the differential equation can be recognized as providing non-linear oscillatory solutions that characterize Lotka-Volterra equations. Without the presence of quadratic terms the predator and prey populations may either exponentially grow to infinity or decay to zero. It is the quadratic terms that model the effect of predation by predators for sustenance and prey population control that lead to non-linear system oscillatory behavior. For a multi-predator-prey problem view of CICD analysis, cell biomarkers can assume the role of both predators and creators of cytokine prey; while cytokine biomarkers can act as the stimulators and suppressors of cellular predation and creation. Homeostasis can provide for the relative population size equilibrium control of all immune system biomarkers. This can effectively enforces system conservation of matter constraints via a least effort process that reflects systemic redundancies, adaptability and robustness. Relative to CICD analysis application patient blood draw data records are coarse and it must be assumed that many un-modeled dynamic immune actions can occur between data sample instances.

Computer System Architecture and Data Modeling Technique

Figure 3:
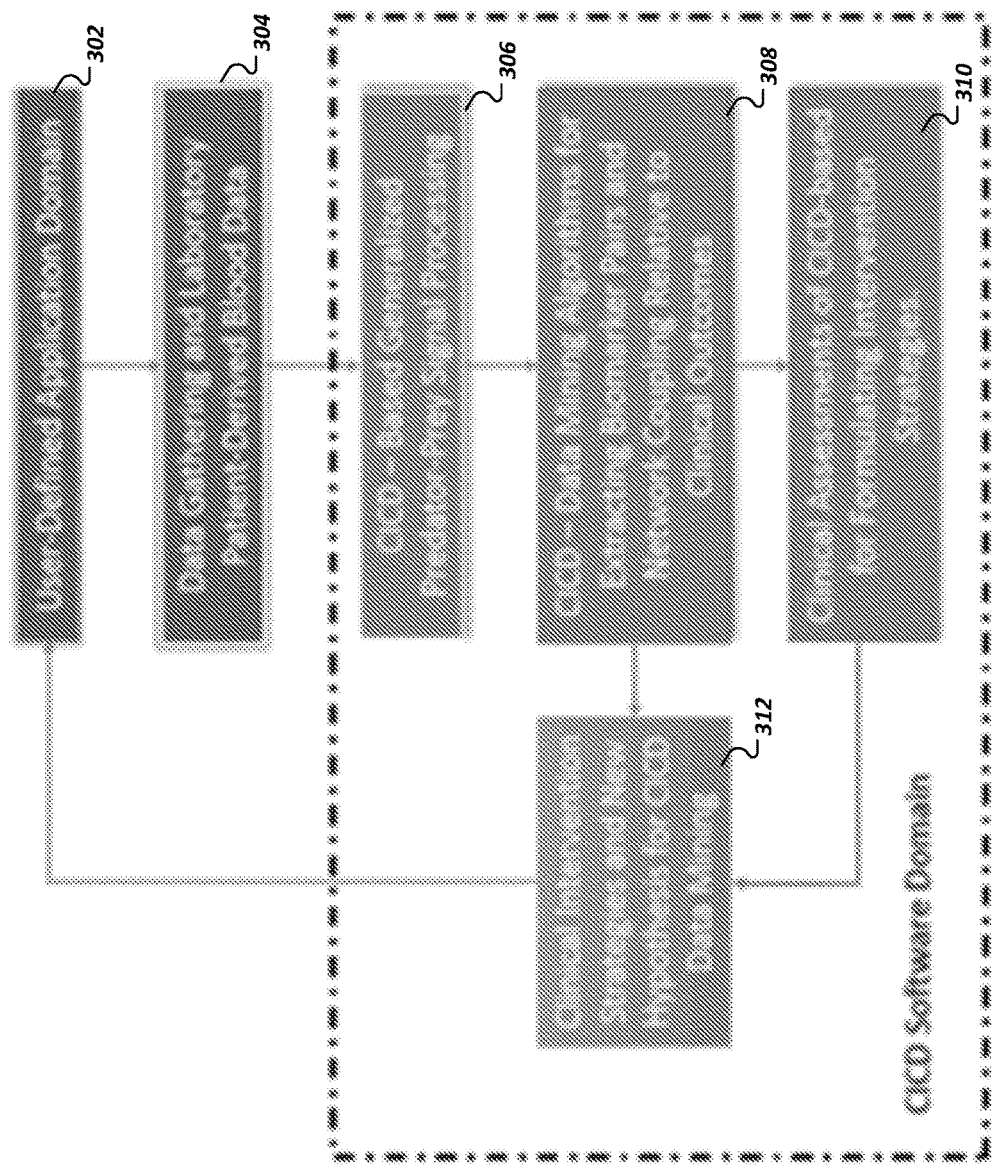
FIG. 3 depicts an example technique for modeling biomarker pairs and using to develop intervention strategies.

As discussed above with regard to FIG. 1, steps in the CICD analysis process consisted of three major sub-blocks of analysis activity: (1) Data gathering including patient blood products and application domain constraints on immune system (biomarker pairs); (2) Advanced signal processing; (3) Data-Mining tools for transforming signal processing data into clinically useful products. FIG. 3 depicts an example technique 300 for modeling biomarker pairs and using to develop intervention strategies. The technique 300 can be similar to the technique 100, described above with regard to FIG. 1, and can be performed by the computer systems described above with regard to FIG. 1, such as the example CICD computer system. The technique 300 can additionally/alternatively be performed by other computer systems that are different from the CICD computer system.

The top 2 blue boxes (302 and 304) in the technique 300 include the front-end CICD analysis process for assembling patient behavior response data and associated system behavior characterization relationships. These steps can completely and unambiguously define systemic behavior relative to the software enabled analysis model. Although steps 302 and 304 are depicted as being outside of the CICD software domain, they may be implemented through computer-based techniques that are performed by a computer system, such as the CICD system.

In the next sequential box (306) signal processing techniques can be performed. Next, problems associated with translating raw mathematical analysis numbers to detail insight can be addressed (308). Lastly problems associated with presenting detail insight views as quantifiable measures supportive of clinical treatment decision-making and analysis enhancement feedback can be addressed (310, 312).

Modeling/Representing the Cause of Biomarker Population Change

Modeling and simulation can gather information about a system to be analyzed and then defines how response evolves. After generating the data, assembling a model for it and executing the analysis process, the next step is to investigate strategies for understanding how the system behaves; i.e., insight discovery. To this end, given system complexity, one seeks whole system decompositions and associated relationships that provide minimally sized sets of partial system views. For example, a partial view can consist of substructures and linear, quadratic, or cubic interaction models. Aggregating and seeing relationships between well-defined partial views lead to insights into global system systemic behavior. Two main sources of information have been used for gleaning this "how-to" modeling insight. First, four years of working closely with Mayo Clinic researchers and clinicians have provided insights for guiding the analysis process. Second, a thorough review of the biological modeling research has identified recurring patterns in the mathematical models used for equivalent CICD analysis capabilities. As a result of this interplay between computational biological modeling, clinically derived insights and the expressed desires for patient data driven analysis based clinical decision making support; a CICD modeling framework has been developed by abductive reasoning that provides results consistent with techniques for validating predictions and justifying continued research along several high value pathways.

During the early phases of this research effort standard commonly used systems engineering decompositions were applied. The first strategy physically decomposed the system using biomarker groupings identified as likely being highly relevant to the CICD problem. This identified a use for a CICD-based knowledge model that would encode all-purpose generic techniques to model only those partial system view components that are biologically meaningful. This can reduce computational problem size and can increase both accuracy and insight by totally removing from the computational process numerical noise associated with the unnecessary inclusion of superfluous information used to model biologically impossible relationships.

Another decomposition strategy can use a nonlinear polynomial representation to provide a decomposed functional representation for the causes of population stimulation and suppression. Such a nonlinear polynomial representation can build on the classical predator-prey interaction paradigm. Immune regulatory processes can be associated with biomarker change decomposed into a mix of time invariant (static), slowly varying in time (quasi-static) and time varying (dynamic) actions. Also, relative to the immune regulatory process and the system physical and functional decompositions can be applied, useful cellular action decompositions can be associated with: (1) tumor invasion of system; observable and modeled cellular response actions triggered and modulated by un-observable, un-modeled systemic causes (tumor and all other cells); (2) system reactions to resource limitations and allocation constraints; (3) cellular response actions stemming from observed biomarker cells triggered by biomarkers and tumor factors; e.g., immune regulatory response to tumor invasion; and (4) immune cell actions stemming from cells having one observable trigger with one or many such modulators. An assortment of non-linear representation expressions for the population change causing actions of cells both triggered and modulated can be used and transformed by series expansion to a common multi-variable approximant polynomial format. Many relevant series expansion candidates exist, such as insight creation and computation need is the Kolmogorov-Gabor polynomial. It can be defined by the sum of all possible constant, linear, bi-linear, tri-linear, . . . state variable product terms each with an unknown coefficient and all collected together into a convergent multivariable Taylor series-like expansion. This polynomial expansion has been used in data mining, pattern recognition, etc. where approximant representations of non-linear functions are required. Conceptually each term in the expansion can be an atomic level component of cause; i.e., biological stimulation and suppression with atomic (finest grain of aggregation) level meaning. As discussed below with regard to the interpretation of all atomic level components have clear meaning; namely, linear terms model the linear growth or decay of observed biomarkers responding to the actions of unspecified cells triggered by observed biomarkers, bi-linear terms model non-linear growth or decay of observed biomarkers responding to specified cellular action triggered by specified biomarkers, tri-linear terms model non-linear growth or decay of observed biomarkers responding to specified cellular action triggered by specified biomarkers and modulated by other bio-markers, etc. This conceptually simple representation model can be used to satisfy the reverse engineering requirement for a hypothesized approximant of population change cause that completely spans the modeling space of relevance with a well-defined order of numerical accuracy.

For example, molecular level components can be created for non-linear Michaelis-Menten kinetics and other such effects by using a summation of atomic linear, bi-linear and (if necessary) higher order atomic tri- and multi-linear terms. CICD's solution process can isolate unknowns associated with all atomic elements within a computable vector of unknowns. It can then place observed biomarker state information and products thereof into associated Kolmogorov dynamic response characterization matrices, as illustrated above in equation 2. The interpretation techniques may be non-trivial and can be made additionally complex by the realization that the set of all possible population change causes are non-linear, partially overlap, and represent resource limitations constraints with immune regulation enabled by triggering, modulation, redundancy, adaptability and least effort execution. It can be the job of the analyst to "see and extract" clinical treatment opportunities from this fully decomposed quagmire of atomic level CICD analysis information. It is at this atomic information analysis level that insight yielding behavior characterization patterns may be clearest and where all computational results can become traceable back to patient specific data records.

Quasi-Static Dynamics of Immune System Cause and Effect

The Equation 3 below provides quasi-static cause and effect dynamics modeling of biomarker population changes through scalar and matrix equations:

$$\left.\frac{d\vartheta_i(t)}{dt}\right|_{t_N} = \square_j(t)\rangle_{t_0} \text{ and } \left\{\frac{d\vartheta}{dt}\right\}\bigg|_n = \{\square\}\rangle_n \quad (3)$$

The symbol $\rangle$ is used to imply a quasi-static dynamics relationship; i.e., the equality defined is true within a short $2\Delta$ time interval $t_s-\Delta < t < t_n+\Delta$ surrounding data sample instant $t_n$ and where $\vartheta_i(t)$—i-th biomarker measured at time t $\{\vartheta\}$—Column vector of all biomarkers at time t $\square_i(i)\rangle$—Causes that stimulate or suppress i-th biomarker change at time $t_n$ $\{\square\}\rangle$—Column vector of all biomarker change causes at time $t_n$ The expression for cause $\square_i(t)$ is approximated by CICD's Kolmogorov-Gabor polynomial adaptation, which is represented in the example Equation 4 as follows:

$$\square_i(t) = \alpha_0(t) + \sum_j \alpha_j(t)\delta_j\vartheta_j(t) + \sum_j \sum_k \alpha_{jk}(t)\delta_{jk}\vartheta_j(t)\vartheta_k(t) + \quad (4)$$
$$\sum_j \sum_k \sum_l \alpha_{jkl}(t)\delta_{jkl}\vartheta_j(t)\vartheta_k(t)\vartheta_l(t) + \dots$$

The coefficients of the constant, uni-linear, bi-linear and tri-linear state variable product terms shown are:

$\alpha(t)$'s—time dependent biomarker interaction coefficients. These are all of the inverse problem unknowns.

$\delta$'s—time independent terms computed directly from the knowledge model, to be described. Associated input data defines all time invariant relationships of biomarker interaction dynamics:

=1, if $\delta$ subscript indices identify a biological possible relationship,

=0, if the relationship is impossible; note, exploitation of this information is critical for minimizing the computational size of the resulting engineering inverse numerical solutions—and—for enhancing model fidelity by inserting expert cause and effect knowledge.

Reverse engineering solution results can provide a dynamics characterization for the whole system within the full $2\Delta$ time interval surrounding the data sample instant.

Relationships between these time instant associated characterizations of quasi-static dynamics provide resultant test period characterizations with clinical decision making value.

Functional View of Atomic Cause Model Elements

To relate Equation 4 to the atomic functional element representations of biomarker change cause, an assumption can be made that, for various time spans used by the CICD system, the tumor factor (antigen) biomarker measure can be constant. It can then follow from recurring bio-modeling patterns identified in reference source equations for the components of population change can cause at CICD's atomic modeling levels; namely: uni-linear terms of the form "aX" can mostly capture biomarker natural growth and decay, the direct consequences of constant sized tumor presence and a linear component of homeostasis driven population growth terms; bi-linear terms of the form "aXY" can mostly capture the nonlinear second order component of homeostasis growth terms that relate to resource limitation constraints and tumor factor stimulation of cellular action; tri-linear terms of the form "aXYZ" can mostly model triggered and modulated immune regulatory command terms. The tri-linear terms can be a core capability within CICD software analysis capability; however, initial proof of CICD concept efforts have focused only on uni- and bi-linear response behavior.

These atomic level behavior groupings can provide decompositions for analysis, visualization, computation and insight development. Furthermore, this approximant representation can provide the framework to approximate population change causes, due to all cellular actions observable by blood draw, without using their explicit enumeration within the Knowledge model's input data file, to be defined.

CICD Implicit Modeling Assumptions

The following modeling assumptions can be used for valid insight development: (a) biomarker measures can be continuous functions within a $2\Delta$ time interval around the data sample instant; behavioral response can be relative to a resultant immune regulatory and homeostasis action; outside of this time interval an unknowable sequence of resultant actions can exist; (b) data sampling and associated interpolation time instances can be coarse relative to cellular action response times; current work infers that $2\Delta$ can be much less than the interpolation time interval of 4 hours; (c) linear interpolation values between sampling instances can provide reasonable estimates for biomarker measures and a smooth transition for all observed biomarker value ratios between the patient data sampling points; (d) no statistical correlation between data interpolation points can be implied or can be inferred from any of the patient data records studied; hence, it can be safe to assume that the set of interpolation points provide random uncorrelated instantaneous views of CICD; it can be further noted that CICD results provide no hint of response continuity between sequential interpolation instances; (e) patient response behavior can be dependent upon the tumor factors associated with the cancer tumor, sized using RECIST measurement standard; (f) biomarker solution vector $\vartheta$ contains observed data; at any time instant, many homeostasis and immune regulatory cellular action commands can be formed, as hypothesized these can be concurrently executed by the immune system using a least system effort strategy to produce all observed data; CICD can use a knowledge model, as defined below, and all observed data to estimate each time instant's whole system command signal and then via the SVD, reverse engineers a dynamics characterization of the observed least effort solution at the time instant; and (g) the number of unknown $\alpha(t)$'s in Equation 3 when expressed in the form of Equation 1, for the whole system command signal, can exceed the number of biomarkers. Hence the CICD matrix inversion problem may have an unbounded number of solutions; however, if the hypothesized principle of least effort is applied then the pseudo-inverse solution can be both unique and it can model the least effort solution; conceptually, the pseudo-inverse solution cam provide a model for this explicitly un-modeled constrained optimization problem.

Knowledge Model and Pseudo-Inverse

Input can incorporate a computer-based "information (knowledge) model" to unambiguously define systemic state based behavior relative to the software enabled analysis model, which can provide an ability to identify all causes that are biologically "possible" and too define the biomarker 5 selector operators of Equation 4. Causes not identified may be modeled as being biologically "impossible". This can provide an analysis capability to explicitly include/exclude classes of cause for analysis focusing, model fidelity enhancement and other such analysis needs. This can allow analysts to use CICD to guide the iterative improvement process that identifies patient and patient group specific response patterns hidden by the spurious noise of biologically "impossible" causes. This cause class can include relationships inadvertently identified as possible and nonlinear contributions that do not adequately model cause driven response observation.

An example knowledge model input data template, extendable for multi-linear models can be represented as:

| Modeling cause and effect. Indices (i, j, k, l) associate math to specific biomarkers | |
|---|---|
| Uni-Linear model | Cause (k) = unknown(k) × biomarker(i) |
| Bi-linear model | Cause (k) = unknown(k) × biomarker(i) × biomarker(j) |
| Tri-linear model | Cause (k) = unknown(k) × biomarker(i) × biomarker(j) × biomarker(l) |

An example implementation of a CICD computer system can use the following illustrative 32 biomarkers: (a) 7 cell types (CD3, CD3/4, CD3/8, CD16/56, CD3/69, CD4/294, CD4/TIM3); (b) 24 cytokine types (FRACTALINE, GM-CSF, IFNa2, IFNg, IL-1b, IL-1ra, IL-2, IL-4, IL-5, IL-6, IL-7, IL-8, IL-9, IL-10, IL-12p40, IL-12p70, IP-10, MCP-1, MCP-3, MIP-1a, MIP-1b, TNFa, TNFb, VEGF) and (c) one constant sized population of tumor factors. Such a CICD computer system can use the above biomarkers to create the following example biomarker population dynamics relationships:

Cell-cytokine, cytokine-cell relationships can be used:
    Uni-linear relationships
        Cell(i) has linear growth from cytokine(j)
        Cytokine (i) has linear growth from cell(j)
    Bi-linear relationships
        Cell(i) has bi-linear growth from cell(i) modulated by cytokine(j) and tumor factors
        Cytokine(j) has bi-linear growth from cell(i) modulated by cytokine(k) and tumor factors
Cell-cell relationships can be used:
    Uni-linear relationships
        Cell (i) has self-linear growth from cell (i)
        CD3.69 has linear growth from CD3
        CD3.4 has linear growth from CD3.69
        CD3.8 has linear growth from CD3.69
        CD16.56 has linear growth from CD3.69
        CD4.294(Th2) has linear growth from CD3.4

CD4.TIM3(Th1) has linear growth from CD3.4
Bi-linear relationships
CD3.3 has bi-linear growth from CD3 modulated by CD3; this is logistic growth
CD4.TIM3(Th1) has bi-linear growth from CD4.TIM3(Th1) modulated by CD3
Cell (i) has bi-linear growth from cell (i) modulated by tumor factors It should be noted that other classes of biomarker population growth impacting (modulating) causes can be implicitly included. For example, cytokines can bind to receptors on immune cells and modulate the secretion of un-modeled enzymes that then fragment modeled cytokines; this class of cause is not explicitly specified in the knowledge model; however, CICD will can "see" it as a sum of two linear relationships: one between the cytokines fragmented by cell secreted enzymes and the other between cytokines that modulate cellular enzyme secretion. Knowledge model relationships can represent the cellular actions that cause respective cytokine population decay, via un-modeled mediators. In like manner, other unknown/unspecified and to-be-discovered population impacting causes can be implicitly included.

Extracting insights from CICD analysis can be a non-trivial process and a topic of continuing research and capability development. For example; the knowledge model currently does not include a model for the internal cellular neural dynamics process of input/output transformation. If the knowledge model indicates that it may not be possible for all cells to secrete and absorb all cytokines then the associated least effort cause and effect response solution is that cellular output is an algebraic function of all cellular input. If it is known that specific cellular/cytokine secretion and absorption relationships will not occur, then these can be excluded to generate higher order modeling fidelity. Inclusion of internal cellular dynamics would require the inclusion of an associated set of cellular state variables along with measures to define creation and absorption time constants. The inclusion of cellular input/output dynamics can be done; however, problem size and viewing complexity would significantly increase. Furthermore, if current research results lead to behavior characterizations consistent with clinical observations and decision making support then it would suggest that neglecting internal cellular dynamics via the algebraic I/O assumption is adequate for a low order clinical decision-making application.

CICD Matrix Equations

Notational condensation of Equations 3 and 4 can yield a non-linear quasi-static matrix differential representation for all possible cause and effect relationships. These can be examined as one large matrix equation—or—as three smaller sized decoupled uni-linear, bi-linear and tri-linear characterization equations, such as those represented in Equation 5 as follows:

$$\left.\frac{d\vartheta}{dt}\right|_n = \lfloor K_U \ K_B \ K_T \rfloor \begin{Bmatrix} \mu_U \\ \mu_B \\ \mu_T \end{Bmatrix}_n \quad (5)$$

$$\left.\frac{d\vartheta}{dt}\right|_n = K_U \mu_U \quad \left.\frac{d\vartheta}{dt}\right|_n = K_B \mu_B \quad \left.\frac{d\vartheta}{dt}\right|_n = K_T \mu_T$$

Equations of this set are linear with respect to all unknowns:
μ's collect all possible Kolmogorov unknowns,
These are all Equation 4 products αj(t)ð̃j, αjk(t)ð̃jk, αjkl(t)ð̃jkl.
K's are 3 rectangular, sparse Kolmogorov characterization matrices that collect all Equation 4 Uni-, Bi- and Tri-linear state variable products.

Once a deeper understanding of the Kolmogorov (KU, KB, KT) characterizations of cause and effect dynamics is obtained via the 3 decoupled equations the one larger equation can be examined; to understand how associated systemic vector resultants are formed, and how insight detail gets lost as decomposition aggregations are formed and applied in analysis before insight can be established. In the application of CICD, differentiation between results based upon Kolmogorov matrix decoupling are adversely weakened by data sparseness and modeling fidelity concerns are possible. CICD can include cross patient statistics based data quality assessment capability. This can be used to identify analysis weaknesses that stem from such atomic level modeling weakness.

Singular Value Decomposition and Modeling Least Effort Control Realization

For CICD problems, the number of biomarkers Nϑ in the vector ϑ can be smaller than the number of unknowns Nμ in the vector (μU, μB, μT). The SVD method can generate the equality represented by Equation 6 below:

$$K = U\Sigma V^T \quad (6)$$

where K is either of the (KU, KB, KT) matrices used separately or together as shown in Equation 5, U is a square order NO matrix of left singular vectors, Σ is a diagonal order NO matrix of singular values and VT is a rectangular Nϑ×Nμ matrix of right singular vectors. The singular values for each equation in Equation 5 equate to the square root of the sum of the squares of all elements in their associated K matrix row. These act in Equation 6 as scaling factors. Each singular value has a left and right singular vector pair and each provides a set of orthogonal coordinates that decompose system resultant cause and effect response behavior into a set of exactly NO natural modes of quasi-static cause and effect behavior per time instant. The singular vectors are orthonormal and can together define the Moore-Penrose pseudo-inverse $K^\dagger$. SVD mathematical identities can be represented as the following in Equation 7:

$$U^T U = 1 \quad K^\dagger = V\Sigma U^T$$

$$VV^T = 1 \quad K^\dagger K = 1 \quad (7)$$

The pseudo-inverse provides the unique 'best fit' (least squares) solution to a system of linear equations. As previously mentioned, this can provide CICD computer systems with an ability to include the dynamics of the un-modeled "least effort" cellular command execution process, without an explicit process model while still fully accounting for the contribution of these effects in the reverse engineering model. The foundational biology assumption implicit in SVD utilization can be that natural selection processes have created action realization algorithms that are realized via least effort (which implicitly provides a unique optimized solution), and that the full set of left singular vectors map the elements of the decoupled modes of behavior to the relative participation measures of all system characterization biomarkers.

CICD Natural Behaviors as Viewed Via Fully Decoupled Modal Coordinates

Insight into a flexible mechanical system's vibrational characteristics can be obtained from its modes of vibration, as characterized by the independent modes recovered via the matrix decompositions used in eigen-analysis. In an analogous manner CICD can develop insight into systemic quasi-static cause and effect behavior via its SVD natural modes of behavior. Mathematically the left singular vectors can relate generalized behavior coordinates q to observable biomarkers $\vartheta$ via the invertible relationships $q=U^T\vartheta$ and $\vartheta=Uq$ while the right singular vectors can relate unknown elements of cause p to the generalized causes Q that drive generalized behavior coordinates q by the invertible relationships $Q=V^T$ and $\mu=VQ$. For CICD insight development, the (KU, KB) Kolmogorov matrices can be used with the diagonal terms associated with self-growth and self-decay removed from KU. By removing these relatively small diagonal elements, numerical noise can be minimized, these removed diagonal elements can be relatively small and add little to characterizing biomarker cross coupling dynamics. Kolmogorov matrices for patient specific state variable data can encode decomposed system dynamics insight, much of which is potentially of value for generating clinical decision making insights. If the set of Kolmogorov matrices are processed together, decompositions can be aggregated and insight can be lost via the non-reversible data processing operations of matrix arithmetic.

Naming Natural Modes of Cause and Effect Behavior

Figure 4A:
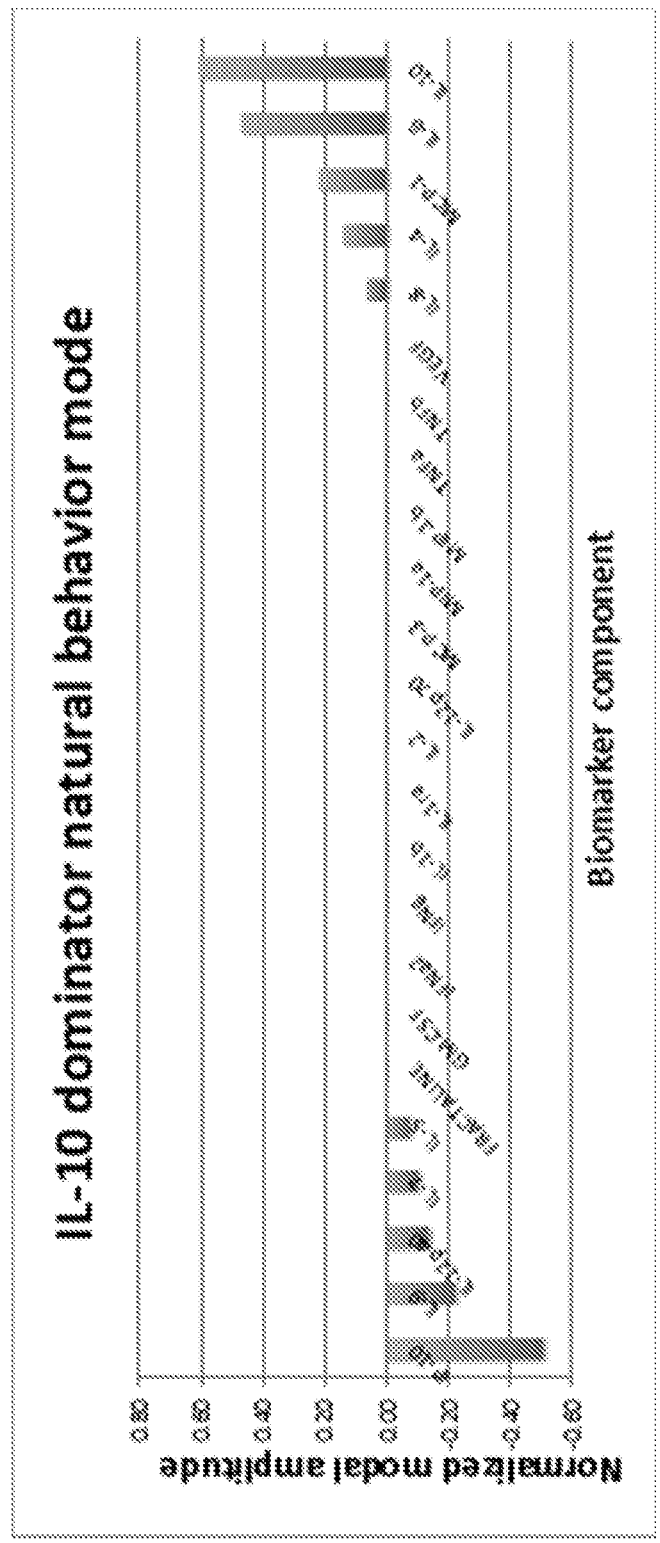
FIGS. 4A-B are graphs that presents two example left singular vectors illustrating unique dominator biomarker nametags being algorithmically assigned to singular values.
Figure 4B:
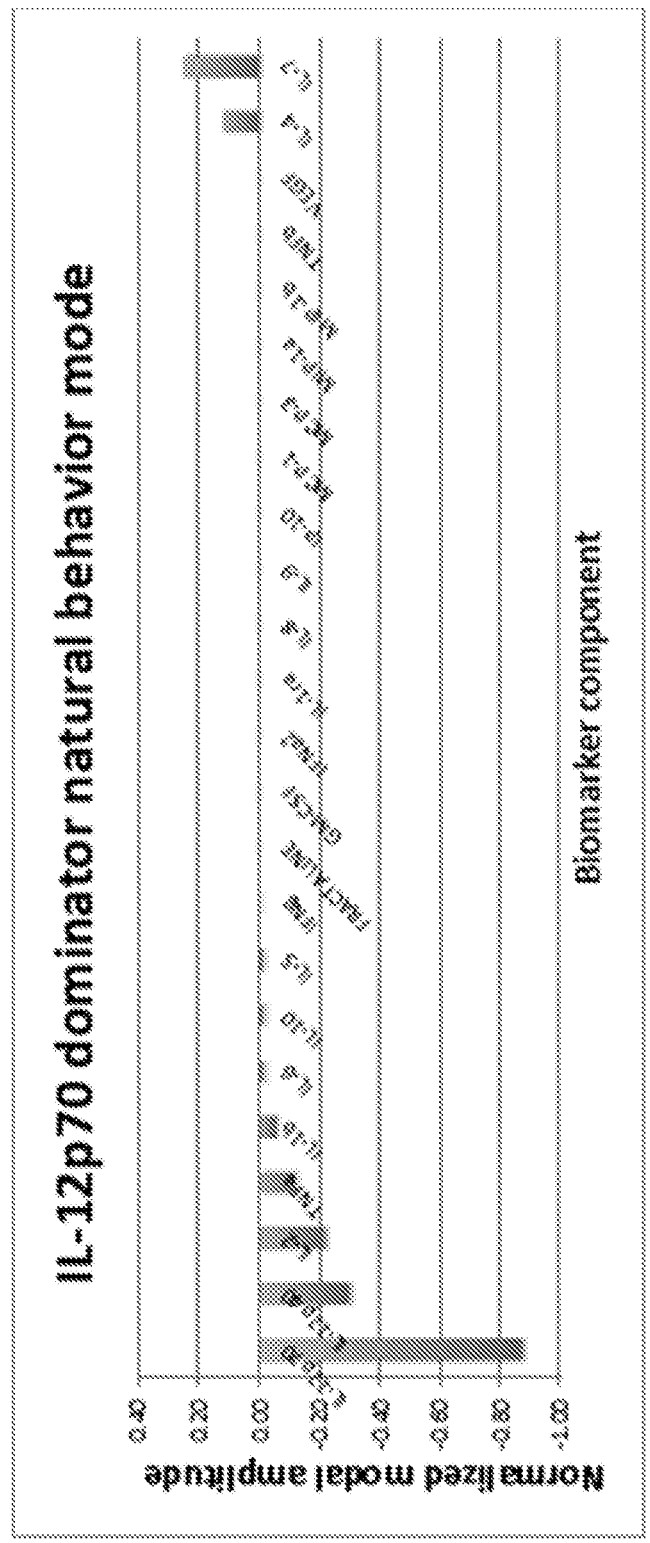

It follows directly from orthonormality conditions and observation that a unique "dominator" biomarker nametag can be algorithmically assigned to each singular value associated left and right singular vector. FIGS. 4A-B are graphs that presents two example left singular vectors illustrating unique dominator biomarker nametags being algorithmically assigned to singular values. The horizontal axis lists biomarker components sorted relative to participation strength: component positive/negative values imply "acts with"/"acts opposite". The nametag assignment algorithm is biased to associate the natural mode of behavior nametag with the biomarker component showing greatest participation strength value.

Figure 5:
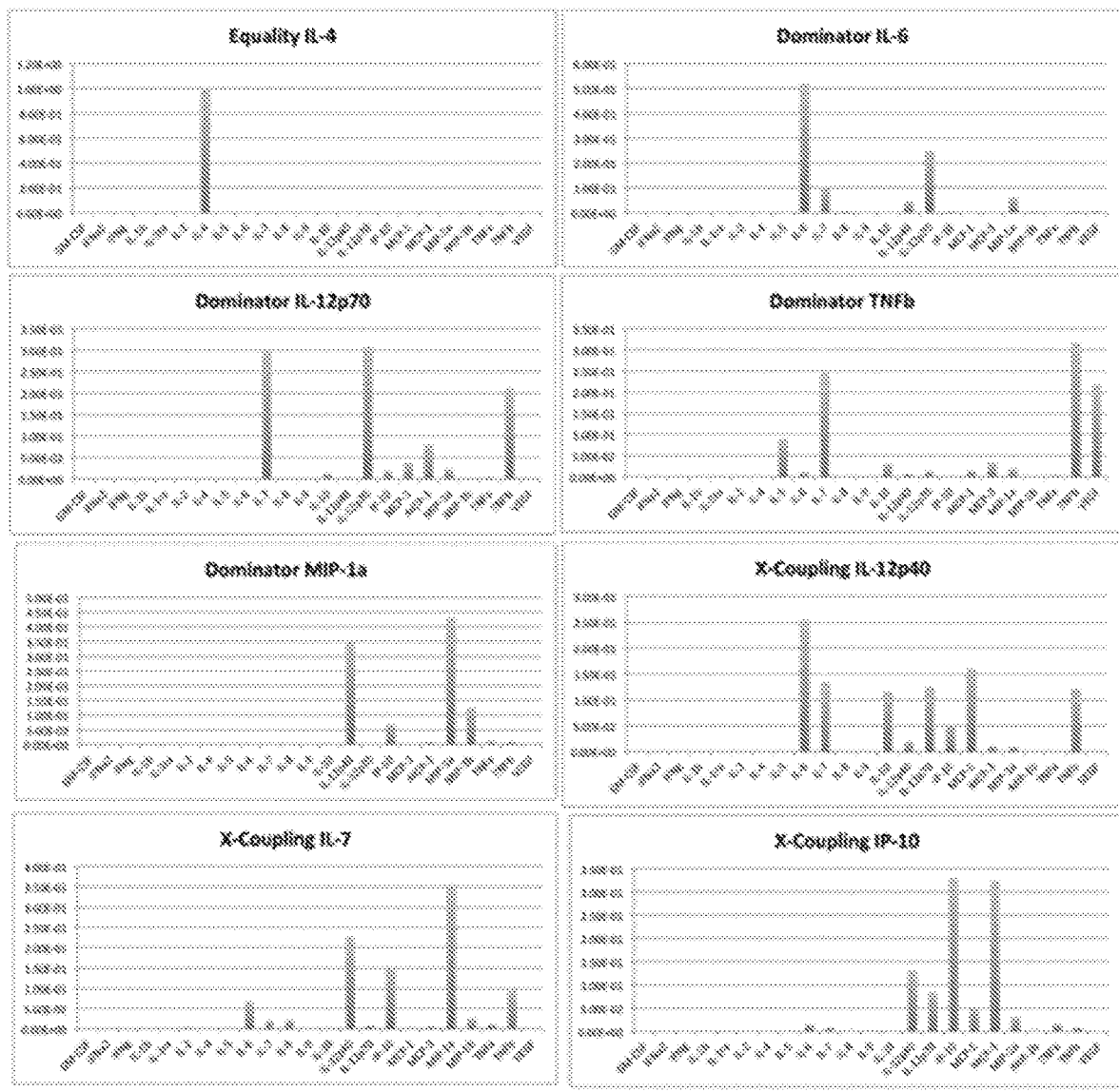
FIG. 5 depicts graphs illustrating example natural behavior mode dominator nametag assignment considerations.

FIG. 5 depicts graphs illustrating example natural behavior mode dominator nametag assignment considerations. Some modes are of "equality" type, these have a dominator clearly identifiable with no supporters. Most modes are of "dominator" type, these modes have an obvious dominator biomarker component with a few supporters of significance. Some modes are of the "X(cross)-coupling" type, these have several support biomarkers of significance without an obvious dominator. For these cases a unique non-redundant dominator nametag is algorithmically defined and applied. The observed coupling provides a visualization of networking operations that support immune command control action.

Natural Behavior Components of Significant Strength Acting Synchronously

Across time instances and patients, the massive reoccurrence of small sized biomarker sets of significant strength, acting synchronously in lock (modal behavior) step per mode, can be taken into account. It is reasonable to hypothesize that these "SyncSets" reflect functional purpose. Unlike electro-mechanical systems that employ minimal degrees of redundancy and effort sharing, the massive number of SyncSets detected across patients and time spans can indicate that redundancy and effort sharing is normal within the human immune system.

An example CICD computational algorithm enables (SyncSet) biomarker modal behavior pairing identification and occurrence counting. For instance, using left singular vector component values squared; pairings can be identified. The squaring operation can transform vector component values into positive percent ratio participation strength measures for each behavior component per natural mode. To identify pairings of significance a participation strength threshold (i.e., a window for observing internal behaviors) can be used, such as a window defined as greater that 0.1 (10%) and less than 0.90 (90%). Left singular vector components within this 10-90% percentile window group can identify pairing sets that contribute significantly to the system's physically realizable effort sharing process: and, hence its dynamics characterization.

Figure 6:
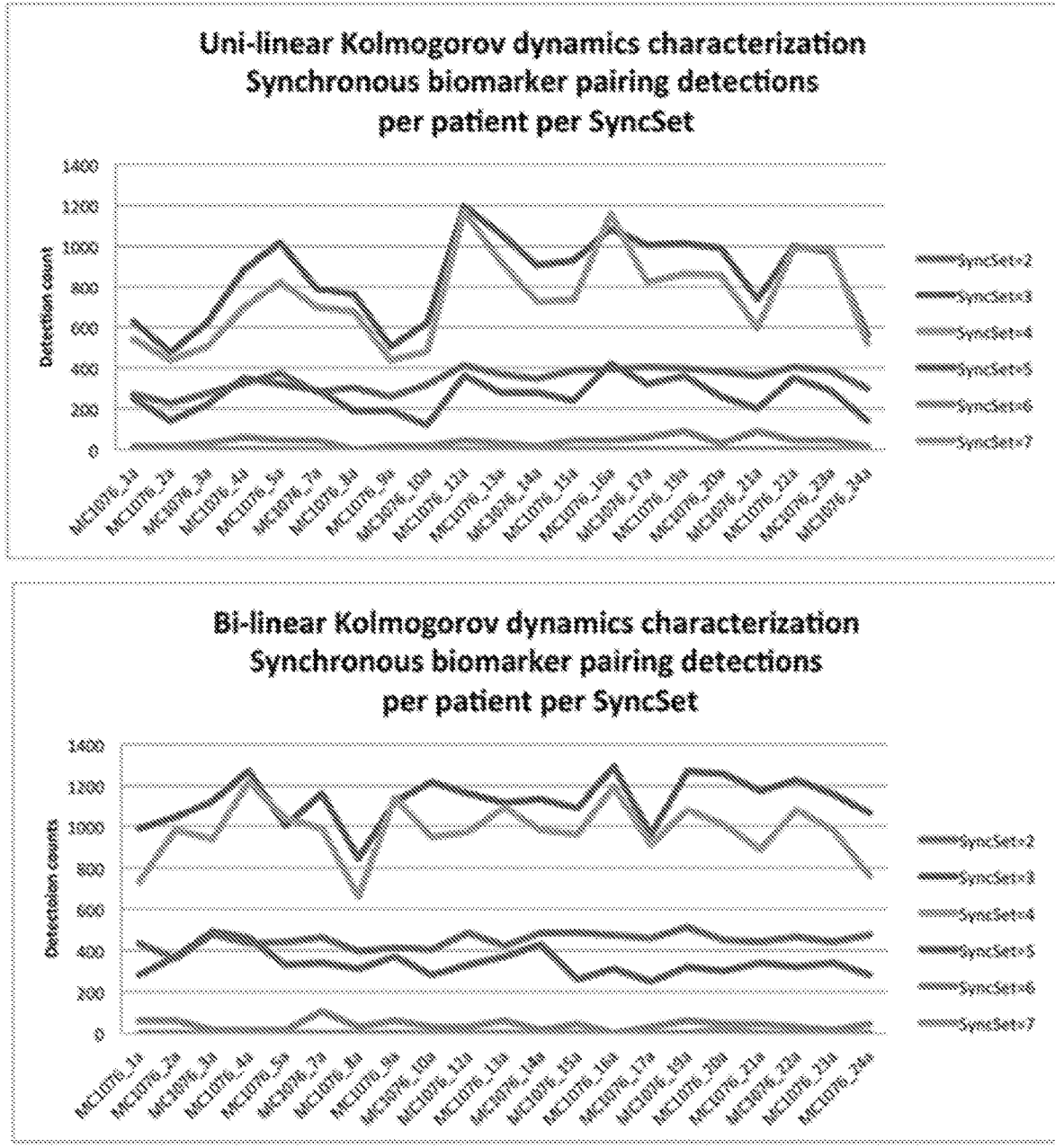
FIG. 6 depicts graphs illustrating examples of how many biomarker pairings are detected per patient per SyncSet size type over a 12-day test period per Kolmogorov dynamics characterization matrix type.

For example, in the example FIG. 4 the IL-10 dominator natural behavior biomarkers IL-10, IP-10 and IL-6 can satisfy the threshold test. These are members of a "SyncSet" of size 3; with three implied biomarker pairings (IL-10, IP-10), (IP-10, IL-6) and (IL-10, IL-6). In the IL-12p70 dominator natural behavior graph, IL-12p70 exceeds the 90% threshold and can have no biomarker pairings. Across all natural modes of behavior, SyncSets of size 2, 3, 4, 5, 6, 7 are possible; these respectively imply associated sets of 1, 3, 6, 10, 15, 21 synchronously acting doublet pairs. FIG. 6 depicts graphs illustrating examples of how many biomarker pairings are detected per patient per SyncSet size type over a 12-day test period per Kolmogorov dynamics characterization matrix type. From these plots a database of nearly 100,000 pairings with associated metadata can be created.

CICD Data Quality Evaluation Via 95% Confidence Intervals

A 95% Confidence Interval (CI) defines a range of values that provide 95% certainty they contain the true mean of the population. Such mean values can be used for the characterization measures used to model CICD, evolve insight and support clinical treatment decision-making. The operative 95% CI relationships are Margin of Error, MoE=1.96σ/n where σ is the data record standard deviation and n is the record length. If m is the record's mean value, then the 95% CI lower bound is m−MoE and its upper bound is m+MoE.

Observed patient data can populate the Kolmogorov characterization matrices in Equation 5 from which SVD generates all singular values and vectors. The first CI utilization step checks quality and cross patient consistency of all data observed and used. From the SVD all biomarker pairings discoverable from left singular vectors can be generated and counted. Again, CI data can be generated for all biomarker pair detections found across all patient records and all time instant natural modes of behavior. This mathematical transformation can have imbedded in it knowledge model relationships defined and listed above. This second CI step can check the quality and cross patient consistency of biomarker pairing data derived from the SVD. This data can be used to define the decoupled behavior analysis space characterized by biomarker pairings and associated strength measures, to be defined. At this step statistical weaknesses can emerge, as should be expected from the sparse data records available and large number of biomarkers included. Here CI data can be used to create a data quality mask to identify and isolate statistically weak results. The data quality mask algorithm can use a weakness threshold test value and either un-normalized MoE or normalized MoE/Mean measures per biomarker pairing; whichever provides the best error amplification.

It is noted that for this example study CI application may not use signal to noise ratio determination methods. Blood draw data records can be available, having 1-day sampling periods are far to coarse for the test based modeling of continuous time views of non-linear CICD rhythmic response behavior.

Example Implementation and Results

Figure 7:
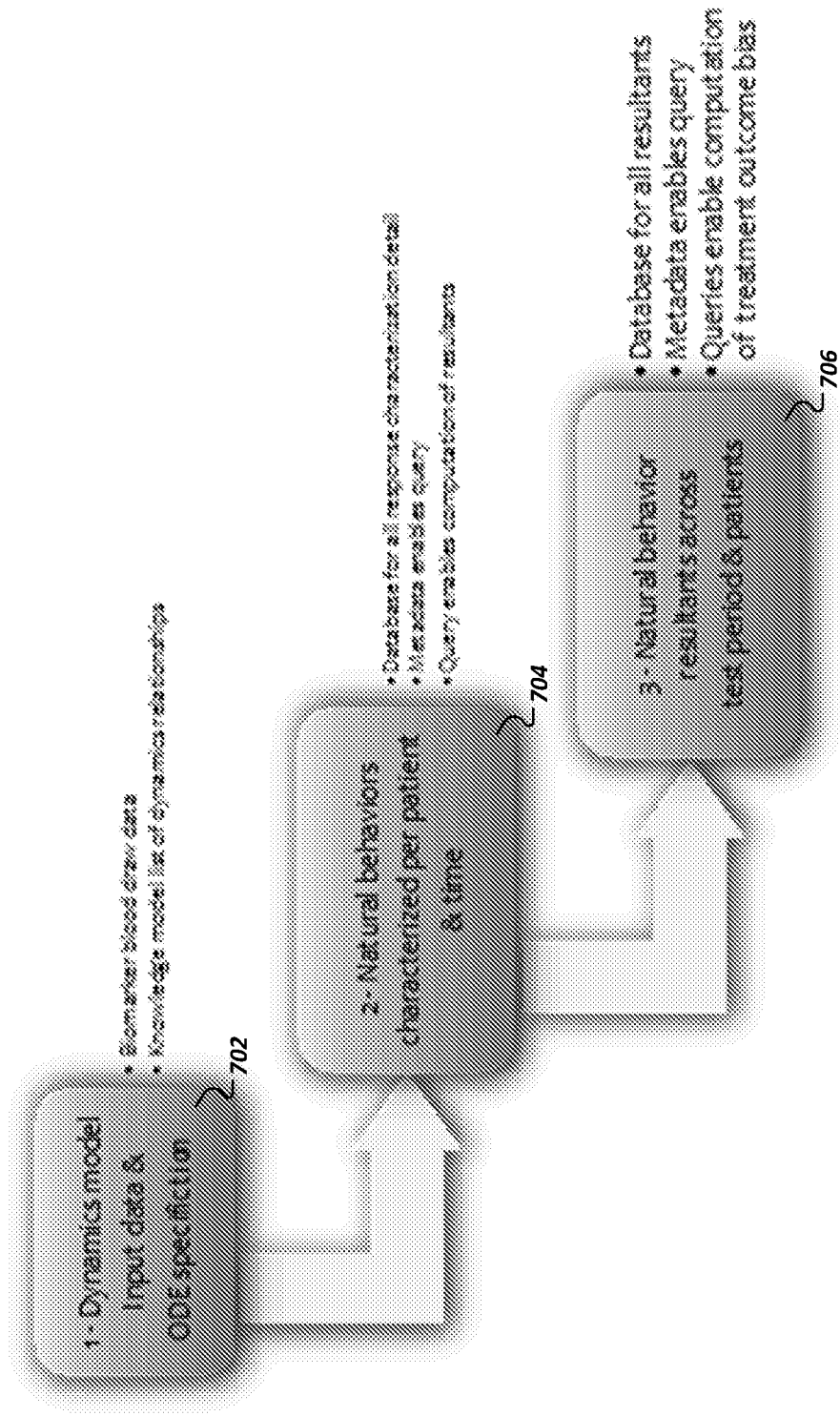
FIG. 7 is a conceptual diagram providing an overview of an example database and metadata for generating data models of systematic immunity.

FIG. 7 is a conceptual diagram providing an overview of an example database and metadata for generating data models of systematic immunity. In box 702, example system dynamics characterization input data is archived. With this data Kolmogorov characterization matrices can be created and decomposed at every patient time instant by the SVD; associated natural behavior data is archived in box 704. This data can then be used to compute resultant patient, patient group and cross time relationships and then archived in box 706. Using all database information and metadata, biomarker pairings that provide primary system function-enabling support can be identified. By judicious arrangement biomarker nametags in a matrix data presentation format one underlying dynamically interconnected immune structure with 3 substructures emerge, of insight development value for all patients, patient groups and biomarker pair characterization measures. Associated values can be used to quantify treatment outcome sensitivity relationships while the structure with substructures view presents outcome sensitivities in a systemic insight rich manner.

The CICD computer system builds upon the mathematical concept of separation of variables. The Kolmogorov matrices K defines the underlying dynamically coupled immune structure as derived from the knowledge model and biomarker time instant population data. The derivative represents rate of biomarker population change and p collects all unknown coefficients for all components of system associated immune and homeostasis cause models.

Insights can be derived from the SVD of K alone. For example, relative to the generalized coordinate space defined by the SVD left and right singular vectors, natural behavior modes describing cell dynamics can be decoupled from those defining cytokine dynamics. Investigations showed that this decoupling is the least effort solution when it is possible for cells to secrete and absorb all cytokines and internal dynamics pathways between cellular inputs and outputs can be ignored. This relationship was not an error. It is a first order fidelity problem view and it is consistent with coarse control system modeling methods used for mechanical engineering control-structure interaction analysis. Coarse modeling methods can begin by using an algebraic input-output relationship that ignores control system complexities and dynamics. Once this model is understood relative to quasi-static control intent, then control dynamics can be modeled and added to the system analysis model.

Biomarker Pairings of Kolmogorov Dynamics Characterizations

An example biomarker pairing identification process can involves 3 example steps: (1) identify biomarker pairs and count associated occurrence detections; (2) identify a measure that reflects participation strength relative to population change causing action; and (3) identify a measure that defines the degree to which pairing nodes "act with" or "act opposite" to each other.

FIG. 5 graphically depicts several typical natural behavior modes and shows the extensive occurrence of synchronously acting biomarkers, with significant participation strength, within specific modes. Characterization data for all SyncSets, previously discussed, and across patients is shown in FIG. 6. Each SyncSet can have a fixed size and contains an associated list of natural mode behavior biomarker components. Together, associated Kolmogorov (KU, KB) case natural behavior data and SyncSet information can leads to the creation of a CICD database containing, for example, nearly 100,000 biomarker doublet pairings with source origin metadata. A database of this size can suggest that biomarker pairings are key to enabling system function execution—and—are the source of clinical intervention opportunities.

Figure 8A:
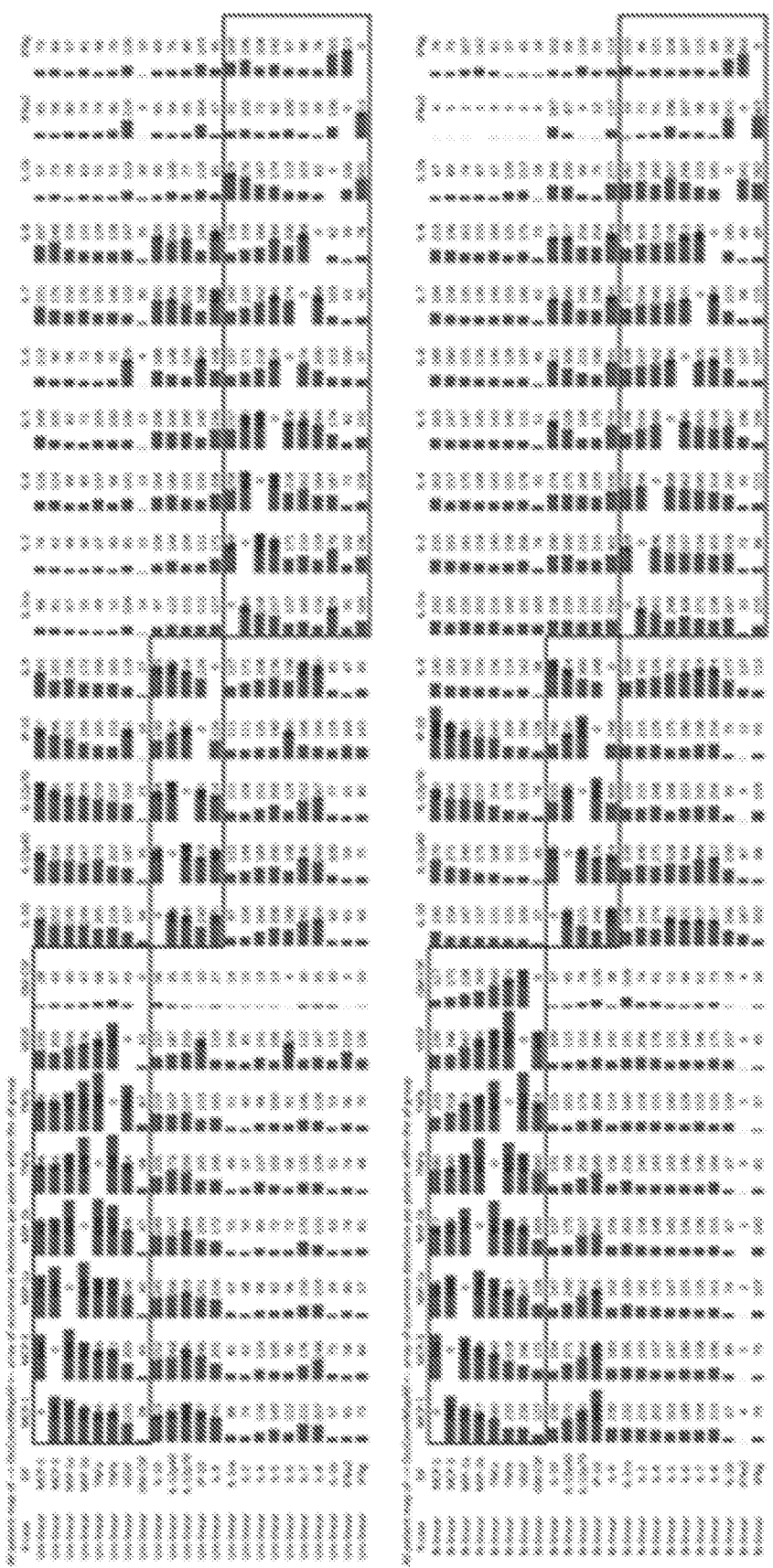
FIGS. 8A-B are tables depicting example occurrence detection count being normalized to occurrence detection counts across all patients per 42 data samples 7 day week.
Figure 8B:
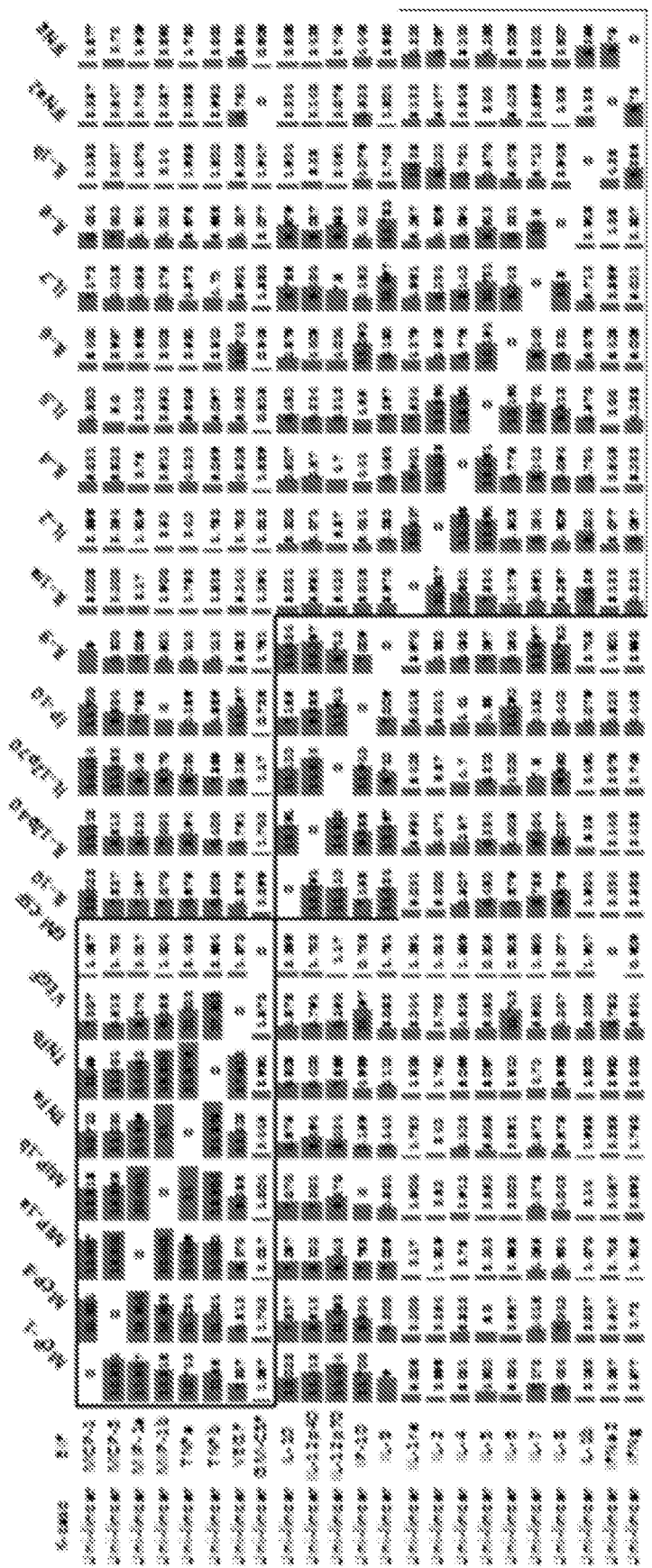

Database query and presentation of biomarker pairing information can lead to large (symmetric matrix maps) of occurrence detection count values for patients and patient groups per Kolmogorov (KU, KB) case. FIGS. 8A-B are tables depicting example occurrence detection count being normalized to occurrence detection counts across all patients per 42 data samples 7 day week. The presentation of large data maps can use a row/column arrangement scheme that supports pattern identification and insight creation. A row/column arrangement algorithm can be based upon occurrence detection count value. This leads to the identification of the 3 boxed cytokine classification groups shown and an insight rich partitioning of biomarker pairs. Mostly, monokine-monokine pairings are identified in this example as having the highest occurrence detection count, these populate the top left (1,1) map partition; mostly, lymphokine-lymphokine pairings are identified in this example as having the lowest count value and are placed in the bottom right (3,3) partition. Cytokines-cytokines in the mid value range support the functional bridging of monokines and lymphokines, these are placed in the central (2,2) partition. Pairings within each diagonal partition reflect similar functional purpose with occurrence detection count values providing a measure that reflects substructure usage frequency. Pairings in partitions (1,2) and (2,3) define monokine and lymphokine couplings that use (2,2) partition biomarkers as bridges to create a functional pathway. Partition (2,3) elements define couplings that enable direct monokine to lymphokine functional pathways. The overall pattern in this example shows that the diagonal blocks have the highest occurrence count values while the off diagonal coupling blocks have uniformly lower occurrence count values. This can be a first step in the evidence accumulation effort to show that CICD results predicted are consistent with immunology expert knowledge and intuition. Note, relative to the current knowledge model system specification cells and cytokines are dynamically decoupled by SVD and hence (cell, cytokine) pairings do not occur. Several (cell, cell) pairings occur (not shown) and these occurrences are consistent with the intuitive expectations of both immunology and knowledge model implied mathematics.

Occurrence Detection Patterns and Insight Inference

Figure 8C:
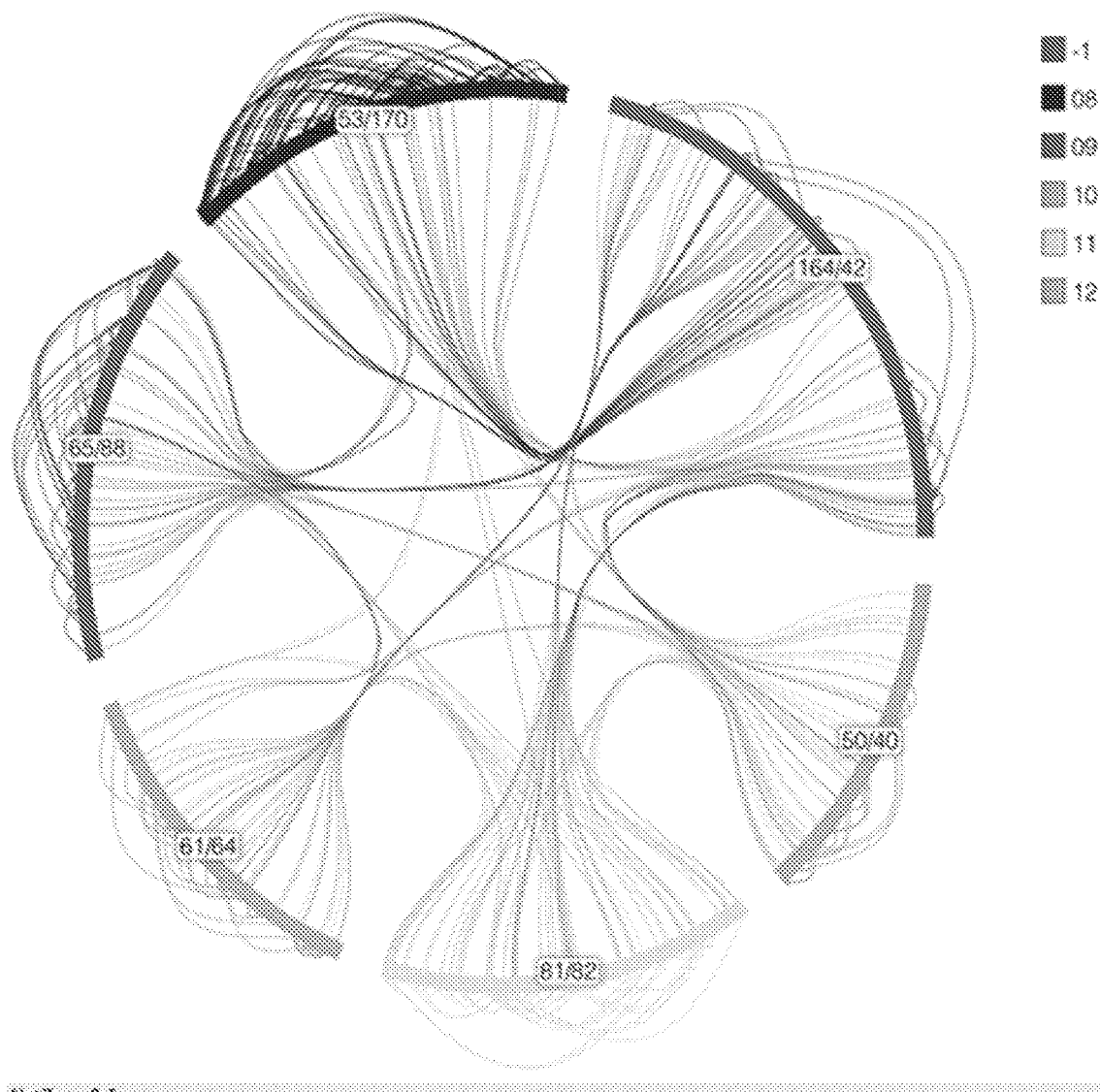
FIG. 8C is a diagram showing an example patient circular network with an array of the count rate per 7 day week mean values per biomarker pairing across patients.

FIG. 8C is a diagram showing an example patient circular network with an array of the count rate per 7 day week mean values per biomarker pairing across patients. Biomarker pairing occurrence count maps can reflect an association between biomarker pairings and function. There is no argument that homeostasis function-based causes are a major driver of population change and that the system's reaction and response to tumor invasion can ripple on any observational signal that views the resultant of homeostasis and immune control. If occurrence detection count maps are viewed from this perspective it can be reasonable to hypothesize that (1) large map values point to the biomarker pairings most active in the causal realization of homeostasis; and (2) small values plus a small component of each large value reflects causal realization of immune control. CICD database query results have indicated this and are hence consistent with a biological view. The large number of different biomarker pairings, all having significant occurrence detection values argue for a massive amount of redundancy that is "homeostasis". Any detectable difference in pairing detection relative to clinical outcome can be likely to be a ripple on top of homeostasis not only because of biological redundancy, but also, because of the very small amount of tumor that exists in a human who still has many more "healthy" organ systems. From these insights; it can follow that clinical treatment outcome biasing discovery will be made most visible by an analysis method that approximates the removal of homeostasis based causes. Since treatment outcome biasing implies the comparison between green (good clinical outcome) vs. red (poor clinical outcome) patient groups it follows that the algebraic operations of subtraction and division, applied to resultant measures, models the removal of homeostasis.

Occurrence Detection Patterns and Confidence Interval (CI) Data Quality Evaluation There can be variability in biomarker occurrence detection values across both time and patients. The statistical quality of all biomarker pairing information can be measured and computed. To normalize this information, a statistical view of occurrence detection counts per biomarker pairing per patient normalized to a 42 data sampling step 7-day week. Note: This may not be a cycles per week frequency measure. It can be however a measure of system behavior rhythm and it can provide an immune controls analysis domain that is close in concept and application potential to the frequency domain as used in classical linear control design theory.

Figure 9:
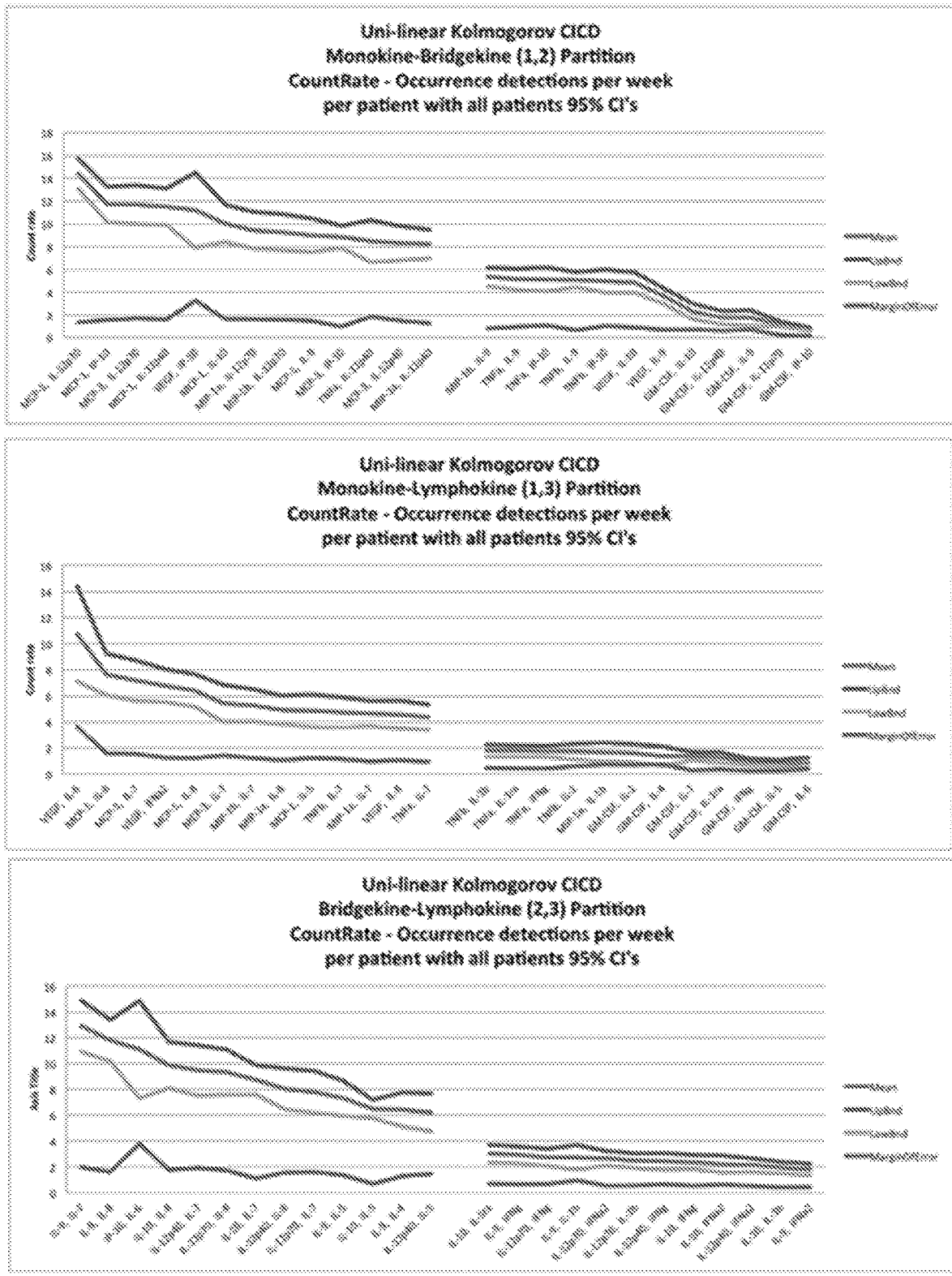
FIG. 9 depicts graphs showing example occurrence detection count values per patient per week are computed across all patients for the Uni-linear Kolmogorov cases.

FIG. 9 depicts graphs showing example occurrence detection count values per patient per week are computed across all patients for the Uni-linear Kolmogorov cases. CI mean values, upper bounds, lower bounds and margins of error measures quantify statistical quality for all pairing mean values and hence the occurrence detection count patterns presented. Plots within this figure are cropped. These only show 25 of the largest and smallest value pairings contained per biomarker pairing map partition mentioned above. Horizontal axes identify mapping partition biomarker pairing labels. Vertical axes identify occurrence detection counts per patient per biomarker pairing per 42 data sample 7-day week. The central gap in each plot spans all partition pairings not identified; for those not listed, values are between the end points shown. These plots are typical for such data; that is, mean values range smoothly from large to small without significant value jumps. The margin of error (MoE) error line is the data quality line. It typically has uniformly low values with some value spikes. Across all plots the spike detection threshold value 0.40 provides a good (strong vs. weak) demarcation value for statistical quality identification. The specific threshold value selected is non-critical. It is used only as a separator for a one-test weakness identification algorithm. Value spikes above 0.40 can both identify weakness and be misleading. Misleading situations are normally easy to detect, are important and provide CICD analysis strength; they dearly point out biomarker pairing anomalies having root causes of special interest. These cases require usage of CICD database query to trace back anomalies to the root cause and insight creation.

Biomarker Pairings, Participation Values and Pairing Node Action Direction

From the perspective of a time domain immune regulatory control process view, both biomarker pair strength and sign can be utilized for immune control command formation and execution. Strength provides intensity to the command control signal while sign can be associated with: (a) selecting stimulative or suppressive functional purpose; (b) enabling coarse immune control via 2 signals that act with each other to find a target or act opposite to each other to stay on target as the target is moved by environmental disturbances; (c) enabling the controller to use natural behavior rhythms to enable least effort rhythm stimulation or suppression. This non-linear immune control vs. linear harmonic electromechanical control design analogy can provide an intuitively exciting research pathway into a deeper understanding of immune control command formation, clinical intervention, stability, robustness and other resultant system response behavior characterizations. Test can be performed using coarse fidelity models for biomarker pairing participation and acting direction measures to demonstrate that patient post-treatment outcome can be correlated with biomarker response characterization predictions derived from pre-treatment blood draw data analysis.

CICD Metrics (Coupling Strength and Sign) for Immune Control Logic

Biomarker pairings supporting functional purpose effort sharing can be detectable by a cellular capability. The 10-90% range window provides a reasonable estimate for such a pairing detection window. Biomarker pairing occurrences collected in the CICD databases are each assigned participation "strength" and a nodes act direction "sign" measure. From this data required model based strength and sign measures can be computed per biomarker pair as follows.

For example, for SyncSets of size 2 associate biomarker pairing members, A and B, form the biomarker pair (A,B) of modal components. Let A and B also represent each respective participation strength value (=modal component value squared). Also, let sign(A)=+1 if the modal component of A is positive and −1 if it is negative. The total resultant participation strength of biomarker pair (A,B) relative to a natural behavior instant is defined as A+B. For SyncSets of size 3 the associate members, A, B, C are used to form biomarker pairs (A,B), (B,C) and (A,C). In like manner, let A, B, C represent respective participation strengths. The participation strength of the biomarker triplet (A,B,C) relative to its natural behavior is defined as A+B+C. The participation strengths of its 3 associated doublet pairs are (A+B)/2, (B+C)/2 and (C+A)/2. Note, the divisor "2" is used to make the sum of the participation strengths of an size 3 SyncSet doublets equal in strength to the root triplet (A,B, C). In like manner, participation strengths for associated biomarker doublet pairings from any sized SyncSet are computed using the divisor (SyncSet size −1).

For all cases the doublet participation strength measure acts as a coarse model of a rhythm-gain measure that would act in the same direction on both nodes. In like manner, a sign measure defined as sign(A,B)=sign(A)×sign(B) provides a coarse model for rhythm-phase. That is, sign(A,B) =+1 if nodes act together and =−1 if they act opposite. System CICD characterization results based upon these 2 measures illustrate that patient outcome biasing determination exists and that the reverse engineering of patient immune control logic via biomarker pairing rhythm gain and phase measure is CICD value added research.

Inferences Obtained from Biomarker Pairing Participation Values

Biomarker pairing participation values can provide a functional purpose intensity measure for correlation and behavior pattern difference explorations relative to green (good clinical outcome) and the red (poor clinical outcome) patient groups.

Patient treatment outcome, as recorded by PFS (Progression Free Survival) time data can be used for patient group assignment. The red group has 14 patients and the green group 7 patients. The demarcation point between groups is 180 days (time to progression). The exploration begins with the computation of mean value participation resultant measures and associated 95% CI statistics for all biomarker pairings. Mean value participation maps for biomarker pairings associated with all Kolmogorov dynamics characterizations cases for both red and green patient groups are generated for large screen viewing.

Within these large maps (not shown) the vast majority of parings were found to have participation measures in the 20-40%, range i.e., between values 0.2 and 0.4. Red vs. green patient group differences are small and consistent with the hypothesis that immune control can be a ripple effect relative to the homeostasis effect. The 20-40% value range of so many participation measures was also found to be consistent with the hypothesis that extensive redundancy and effort sharing is normal for human systems. Low participation measures per pairing implies that 2,3,4 pairs are typically involved in effort sharing; higher values would imply that the pair mostly acts alone or at times with one other; these cases are relatively rare. All of the above is consistent with commonly held immunology knowledge and further supports CICD modeling validation.

Clear and obvious evidence of participation biasing via participation maps was not found; again this implies that the immune control of biomarker population can have a ripple effect masked by homeostasis. The search for participation biasing evidence uses a green vs. red patient comparison method with homeostasis removed. The algebraic operation of division models the approximate removal of the homeostasis and makes the ripple effect of immune control visible.

Participation Value Biasing Seen by Removal of Homeostasis Component

Figure 10:
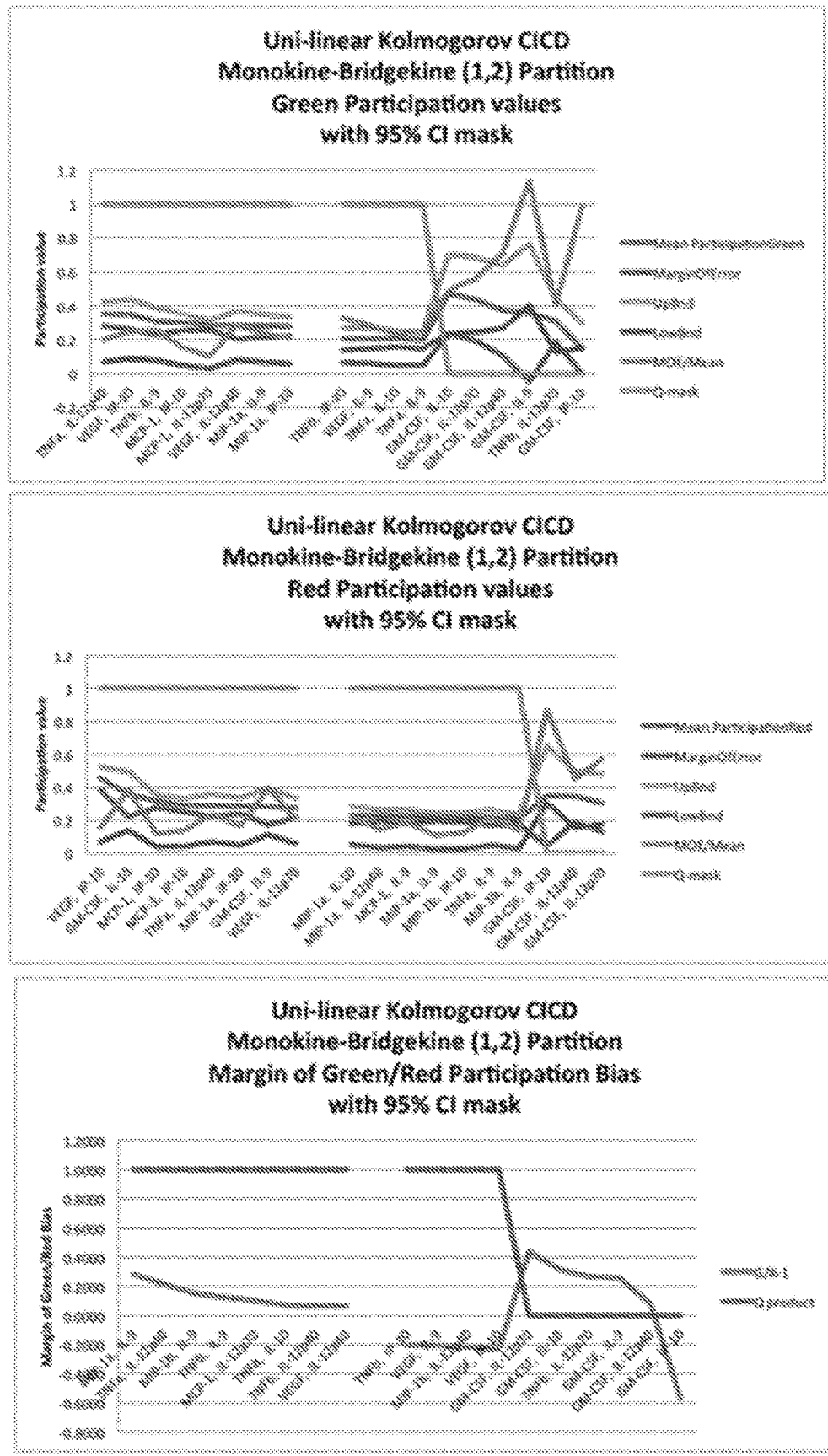
FIG. 10 depicts graphs provides an abbreviated view of example data generated and used for participation value patient outcome biasing and rank ordering for the Uni-linear Kolmogorov case.

FIG. 10 depicts graphs provides an abbreviated view of example data generated and used for participation value patient outcome biasing and rank ordering for the Uni-linear Kolmogorov case. The depicted example data was generated for the 6-biomarker mapping partitions defined earlier. Data computed includes green and red patient group participation mean values along with 95% CI data for upper and lower bounds along with (MoE) and normalized (MoE/Mean) measures that amplify the MoE measure and thus provide a better data quality measure. The data quality mask specification used is: mask value 1 implies that the pairing's CI MoE/Mean measure is less than test threshold value 0.4; mask value 0 implies test failure. In figure Rev 5.10 mean participation values for both green and red patient groups for biomarker pairings with highest values and all pairings that fail threshold testing are shown for the (1,2) partition. The data gap is associated with all pairings in the (1,2) partition not listed on the horizontal axis, their values are between the end points shown. This data typifies that of all other partition data sets. The last graph of each figure set plots margin of participation bias vs. biomarker pair name. It is defined as: (green participation value)/(red participation value)−1.0. This relationship computes a % ratio measure for viewing Green/Red biasing when the homeostasis component is approximately removed by the algebraic operation of division. Positive values measure green % ratio bias, negative values measure red bias.

Summarization of Participation Value Biasing Results

Example Table 1 (below) depicts example data extracted from a CICD database represented in FIG. 10 and the other partitions, not shown, providing a summary list of all uni-linear case pairings with margin of participation biasing greater than 25% (i.e., last column absolute value greater than 0.25) along with associated pairing participation and 95% CI data quality measures for both green and red patient groups. The example pairings in Table 1 are rank ordered, for correlation with biological knowledge and CICD capability validation. Data ranking is based upon mathematical considerations that form a balanced maximization of margin of participation bias % ratio values and minimization of associated green and

TABLE 1

Uni-linear biomarker pair participation value list rank ordered

| Kcase | Partition | | Rank order | Green Participation | Green MOE/Mean | Red Participation | Red MOE/Mean | Participation Green/Red-1.0 |
|---|---|---|---|---|---|---|---|---|
| Uni-linear | (1, 3) | TNFb, IL-8 | 1 | 0.2955 | 0.1252 | 0.187 | 0.1345 | 0.5802 |
| Uni-linear | (1, 3) | MIP-1b, IFNa2 | 2 | 0.3969 | 0.2902 | 0.2468 | 0.2236 | 0.6082 |
| Uni-linear | (3, 3) | IL-1b, IFNa2 | 3 | 0.4796 | 0.2626 | 0.3218 | 0.2442 | 0.4904 |
| Uni-linear | (1, 3) | MCP-3, IL-8 | 4 | 0.4447 | 0.2687 | 0.3202 | 0.1724 | 0.3888 |
| Uni-linear | (1, 3) | TNFa, IL-2 | 5 | 0.3631 | 0.3784 | 0.2201 | 0.17 | 0.6497 |
| Uni-linear | (3, 3) | IL-4, IL-6 | 6 | 0.3652 | 0.1896 | 0.2676 | 0.2396 | 0.3647 |
| Uni-linear | (2, 3) | IL-12p70, IFNa2 | 7 | 0.3005 | 0.2652 | 0.2068 | 0.2587 | 0.4531 |
| Uni-linear | (2, 3) | IL-12p70, IL-5 | 8 | 0.1905 | 0.2817 | 0.2775 | 0.176 | −0.3135 |
| Uni-linear | (1, 3) | TNFa, IL-1ra | 9 | 0.1441 | 0.2478 | 0.2095 | 0.2018 | −0.3122 |
| Uni-linear | (1, 2) | MIP-1a, IL-9 | 10 | 0.2831 | 0.239 | 0.2204 | 0.1098 | 0.2845 |
| Uni-linear | (1, 3) | MIP-1b, IL-1b | 11 | 0.3041 | 0.3563 | 0.1964 | 0.2723 | 0.5484 |
| Uni-linear | (1, 3) | TNFb, IL-4 | 12 | 0.2075 | 0.2574 | 0.2975 | 0.1727 | −0.3025 |
| Uni-linear | (3, 3) | IL-1ra, IFNg | 13 | 0.2298 | 0.2525 | 0.3205 | 0.1247 | −0.2830 |
| Uni-linear | (1, 1) | TNFa, GM-CSF | 14 | 0.4632 | 0.3539 | 0.2335 | 0.3557 | 0.9837 |
| Uni-linear | (1, 1) | MCP-3, GM-CSF | 15 | 0.1819 | 0.3842 | 0.3098 | 0.2576 | −0.4128 |
| Uni-linear | (1, 1) | MIP-1b, GM-CSF | 16 | 0.1466 | 0.3032 | 0.2456 | 0.3341 | −0.4031 |
| Uni-linear | (3, 3) | IL-8, IFNa2 | 17 | 0.1874 | 0.1999 | 0.2896 | 0.3694 | −0.3529 |
| Uni-linear | (2, 3) | IL-12p70, IL-1b | 18 | 0.1715 | 0.2168 | 0.2479 | 0.3008 | −0.3082 |
| Uni-linear | (1, 3) | TNFb, IL-6 | 19 | 0.194 | 0.2832 | 0.3148 | 0.3393 | −0.3837 |
| Uni-linear | (2, 3) | IL-12p40, IL-4 | 20 | 0.3675 | 0.3771 | 0.2661 | 0.2272 | 0.3811 |
| Uni-linear | (2, 3) | IP-10, IFNg | 21 | 0.4086 | 0.3784 | 0.2914 | 0.2991 | 0.4022 |
| Uni-linear | (3, 3) | IL-1ra, IL-6 | 22 | 0.2348 | 0.2253 | 0.3529 | 0.3643 | −0.3347 |
| Uni-linear | (1, 3) | MCP-3, IL-7 | 23 | 0.2004 | 0.2343 | 0.2736 | 0.2672 | −0.2675 |
| Uni-linear | (2, 3) | IL-12p70, IL-2 | 24 | 0.1392 | 0.2366 | 0.2003 | 0.3548 | −0.3050 |
| Uni-linear | (1, 3) | TNFa, IFNa2 | 25 | 0.3671 | 0.3208 | 0.2907 | 0.2596 | 0.2628 |

TABLE 1-continued

Uni-linear biomarker pair participation value list rank ordered

| Kcase | Partition | | Rank order | Green Participation | Green MOE/Mean | Red Participation | Red MOE/Mean | Participation Green/Red-1.0 |
|---|---|---|---|---|---|---|---|---|
| Uni-linear | (2, 3) | IL-12p70, IL-4 | 26 | 0.2623 | 0.3532 | 0.2091 | 0.1612 | 0.2544 |
| Uni-linear | (2, 3) | IL-10, IL-1b | 27 | 0.1842 | 0.3372 | 0.2645 | 0.3451 | −0.3036 |
| Uni-linear | (1, 3) | MIP-1a, IL-1ra | 28 | 0.1793 | 0.3314 | 0.2512 | 0.3755 | −0.2862 |

Figure 11:
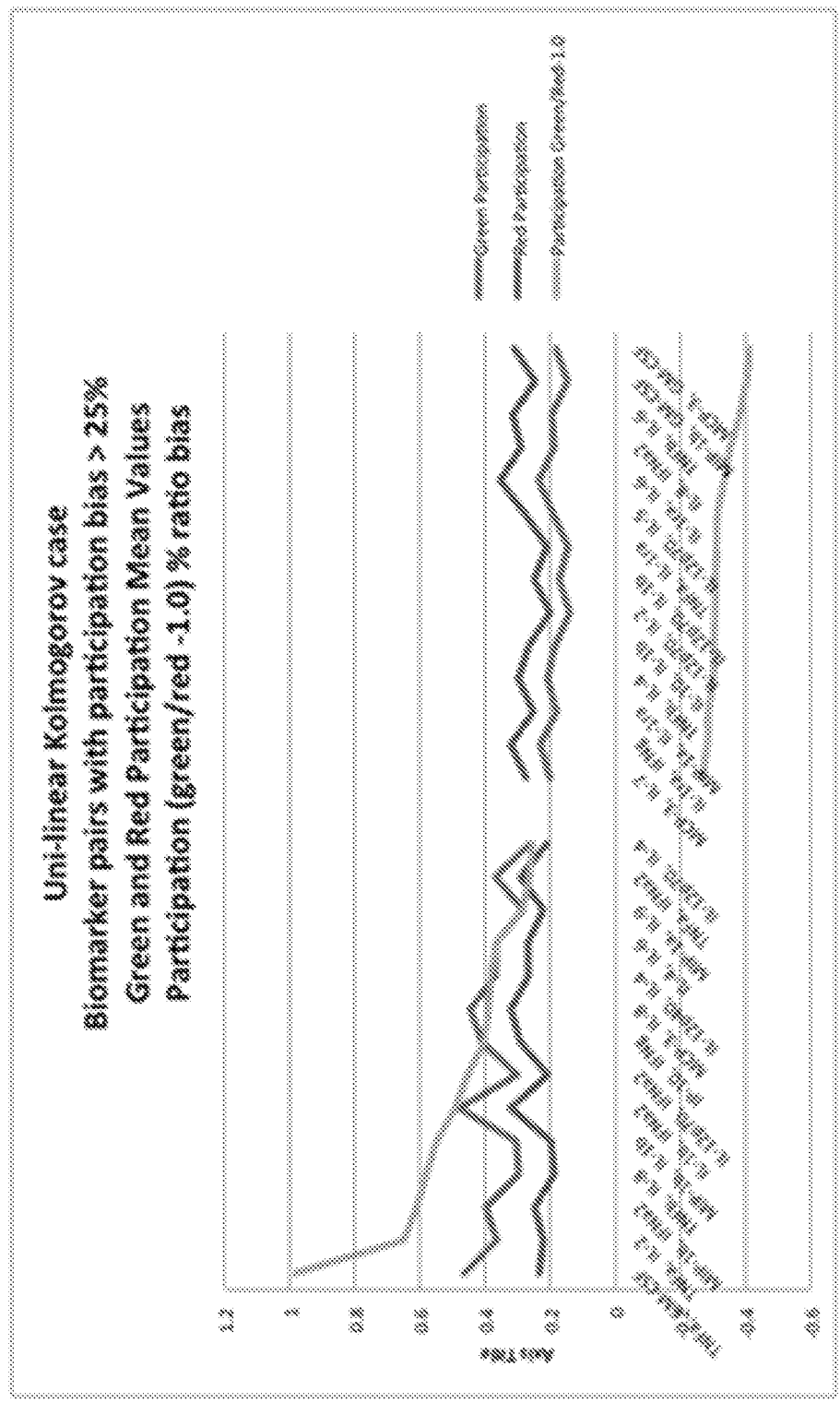
FIG. 11 depicts a graph displays the example data from Table 1.

FIG. 11 depicts a graph displays the example data from Table 1. This example graph contains respective biomarker pairing participation values for red and green patients along with the associated participation bias % ratio measure. Note that only a few pairings have stand out biasing value. Given the high degree of redundancy and effort sharing that exists within the human immune system this is consistent with expectations.

A comparison of these pairings with database pairing occurrence count detection data shows that the pairings listed have occurrence detection count rate values, high enough, to pass 95% CI data quality testing. However, count rate values are modestly low, and within this set, only a few pairings having biasing % ratio values (column 9) much above 30%. That is, few pairings have large participation bias values and most of these have modestly low occurrence counts. This observation supports the hypothesis that participation intensity alone cannot enable a least effort immune control action. Rational: 1) Only a very few pairings across all time and all patients within the 2 week test window show significant bias, the implication is that active immune control of participation value alone cannot be an effective control option; 2) high occurrence detection pairings do not exist, hence these cannot be a least error control solution and 3) low occurrence detection pairings control have minimal effectivity. From these 3 observations, the abductive inference is that the effectivity of immune control action is not via the control of biomarker pairing participation intensity alone; but, also via the control of the command action direction of associated pairing nodes.

Biasing of Biomarker Pair Nodal Action Direction

If, the immune system indicates that the homeostasis process acting across the whole human system is close to random, then process biasing with phasing provides an exploitable least effort mode of immune control. This would be a slow response process, as it would be a ripple level perturbation added to a much stronger resultant homeostasis action. To investigate this acts direction component of the hypothesis, a coarse model designed for concept exploration is used.

Figure 12:
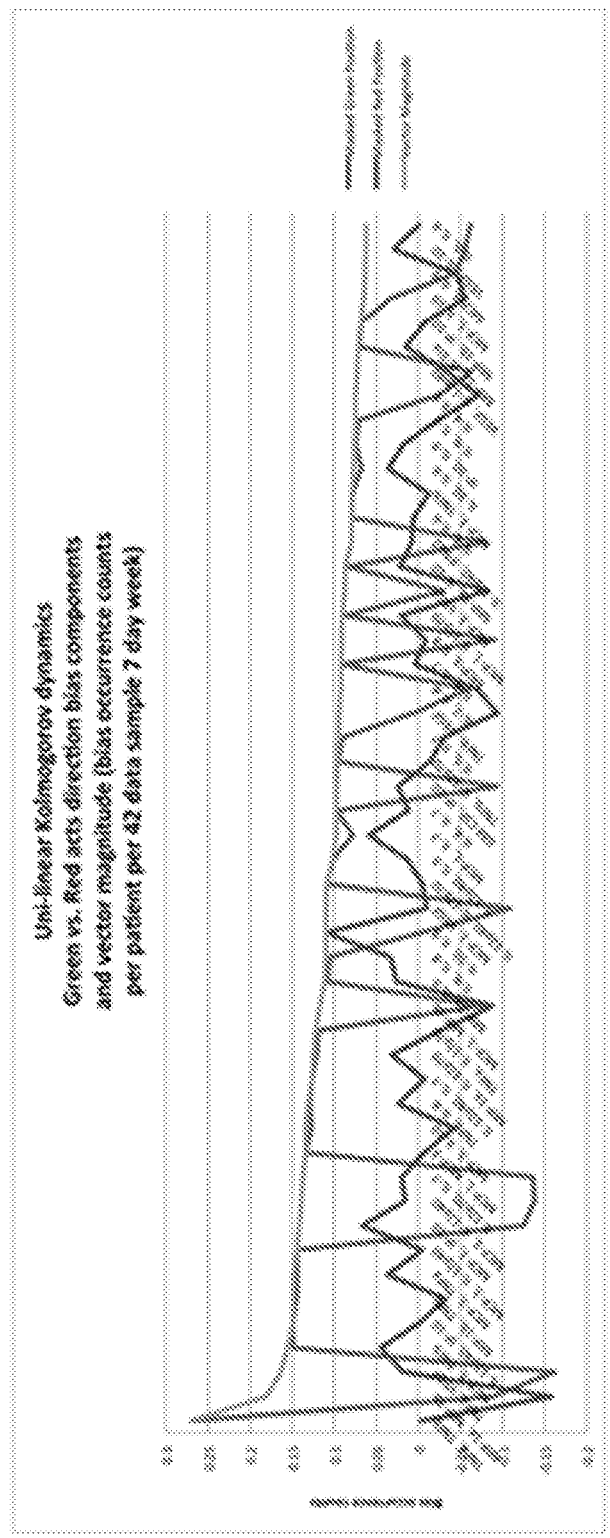
FIG. 12 depicts a graph showing these example results for the top 50 most biased biomarker pairings relative to the green and red patient groups.

An example model to do so ignores nodal participation intensity values by only assigning the +1 or −1 "sign" value to every biomarker pair. The sign measure sign(A,B)=sign (A)×sign(B) leads to the coarse nodal pair acts direction model for rhythm-phase. Aggregation of sign(A,B) values for a (A,B) pair across time instances and patients provides a measure for the (A,B) pair's resultant deviation from the homeostasis zero mean value of pure randomness. The algebraic process of subtraction approximates the removal of homeostasis; accomplished by division in the preceding participation value study. Again, 95% CI methods are first used to access statistical data quality across all, green and red patient groupings. Results are then filtered via two threshold measures. One removes pairings that have bias values near zero and the other removes statistical weak pairings. FIG. 12 depicts a graph showing these example results for the top 50 most biased biomarker pairings relative to the green and red patient groups. Green patient bias, red patient bias and an associated vector magnitude of green minus red component bias measures are plotted for each pairing. Bias values are normalized to measure detection counts per patient group patient per 42 data sample 7-day week. This figure shows that many biomarker pairings have biasing values of significant magnitude and that values are uniformly greater for the green patient grouping relative to the red grouping. This observation suggests that many biomarker pairings will have detectable green vs. red patient outcome biasing relative to immune acts direction (rhythm-phase) control commanding. It also demonstrates that rhythm-phase should be clearly detectable by reverse engineering; and, that it is an integral part of the immune control process.

From these figures several observations can be made: 1) Many biomarker pairings have near zero detection bias and fail threshold testing; this is consistent with the hypotheses of homeostasis randomness and immune control ripple biasing across all biomarkers. 2) Threshold demarcation lines show the exclusion of many more pairings than for participation values. Rationale: lower occurrence detection counts per case leads to data quality weakness. 3) Across all red vs. green patient group plots, mean value measures for "acts with" and "acts opposite" direction measures are significantly greater for green than red patients, which can be seen in FIG. 12.

While a clear behavior pattern exists to support expectations, deeper CICD analysis detail reveals that superfluous response data can mask actionably information. The knowledge model assumption that cells absorb and secrete all cytokines can add superfluous information and contaminates the process of homeostasis removal by algebraic subtraction. Node participation intensity was neglected, this omission would amplify error in the algebraic subtraction process. The availability and application of such abductive inference data for CICD results assessment cannot be under-estimated. This exercise clearly demonstrates CICD's ability to not only detect statistical weaknesses in results but too also point the analyst to where model weaknesses exist and how they can be resolved. This is a useful complement to the iterative improvement spiral upon which research and the scientific method relies. The search for actionable can act direction biasing information is a subject of ongoing research.

Results Summary

Based only upon daily blood draw biomarker data from an example set of 22 patients taken daily for a 2 week test period and the hypotheses that the rate of change of biomarker populations is equal to the sum of all causes, that all causes can be approximated by a convergent polynomial expression and a knowledge model that can identify biologically impossible elements of cause. The following example results have been determined from the computer-based techniques and systems described above:

Patient blood draw data can be used to reverse engineer details of human immune control system actions as executed CICD analysis data-based characterization information enables many relationship queries that together lead to clinical intervention insight and decision making support.

Biomarker cause and effect dynamics characterizes a time varying behavior response structure with substructures.

It is definable from the system natural behaviors that characterize a multivariable predator prey system with non-linear oscillatory response behavior.

Expert knowledge of cellular-cytokine cause and effect relationships can be specified. A reusable database of all such relationships for all cells and cytokines of CICD relevance needs to be created and validated by extensive literature search and laboratory testing.

Natural behaviors are characterized by a small set of biomarkers of significant strength, acting synchronously in lock (modal behavior) step per mode.

Specific biomarker pairings act with such frequency, across all time and all patients that it is reasonable to hypothesize that they concurrently support both homeostasis and immune regulatory action.

Biomarker pairings can be grouped so as to characterize

Three dynamically coupled behavioral response substructures with time varying, patient specific, quasi-static characterization Mathematical views, as matrix maps can be defined Intuitive views, as circular networks can be defined Biomarker pairings are the actuation control elements of the immune regulatory process. They are controlled via immune regulatory actions that create a ripple perturbation acting on and concurrently with homeostasis actions Just a mechanical systems use natural modes of vibration to provide least effort control for vibration suppression, the immune regulatory system is hypothesized to use non-linear homeostasis rhythms to provide least effort immune regulation of biomarker growth suppression and stimulation Gain and phase control measures of linear harmonic control design analysis theory provides analogies that can be exploited for immune regulatory system analysis Biomarker pairing response based outcome biasing measures exist Associated 95% CI measures are obtainable for statistical data strength or weakness assessment These are indicative of what can be monitored, quantified, compared and used for clinical treatment decision making Conclusions The results presented herein have demonstrated that it is feasible to apply and extend CICD computational software to quantify reverse engineering views of the immune regulatory system's cause and effect dynamics with an order of precision necessary to provide both clinical intervention response insight and clinical treatment decision making support. Furthermore, CICD software provides abilities to access computational results statistical strengths and weaknesses and provide guidance for model refinement identification, specification and associated modeling insertions into CICD's scientific method iterative improvement spiral.

FIGS. 13-21 and the corresponding description, and the description in the proceeding paragraphs depict/describe features that can be implemented as part of, in combination with (and/or in any possible subcombination with), separately from, and/or as substitutes to features described above with regard to FIGS. 1-12. For example, the featured described with regard to FIGS. 13-21 can be used alone, in combination with, and/or as substitutes to the features described above with regard to FIGS. 1-12.

Materials and Methods: Overview of Mathematical Modeling

Some previous methods of mathematical modeling have applied assumptions that create simplified views of biologic (immune) system behavior that highlight a specific component's response that is intuitively judged to be of primary concern. Unfortunately intuition failures can be introduced and an iterative model improvement cycle can follow. This is the classical spiral development process of systems engineering. For complex Ill-defined systems (such as systemic immunity in patients with cancer) the iterative improvement process is a non-trivial process that seeks to minimize model complexity while also maximizing model value. As model complexity increases and analysis performance remains static one may abandon the assumption that an a-priori model for an interconnected set of such models can be defined, it is the inherently simplified nature of modeling assumptions applied that can set up barriers to generating additional technical insights. Unlike statistical analysis that works with many randomly collected data instance information sets, or predictive analysis that works with differential equations that define laws of nature; reverse engineering can uses approximate differential relationships consistent with accepted biological knowledge and the assumption that system transitions between serially collected data instances can be approximated. This model for system interaction dynamics can have an infinite number of measured and interpolated data points available to compute a complete time record for an approximate model for cause and effect system dynamics. The example CICD analysis process produces and systems described in this document provide insight on rich characterizations for system biomarker interactions, consistent with well establish and plausible biological knowledge.

Engineering model realization can lead to the formulation of an inverse problem that maps observed response to a hypothesized systemic behavior representation model rich with insight potential. CICD can exploit the realization that the purpose of computation is insight, not numbers. Analysis method selection can be based upon bedrock technology. From the perspective of system analysis for scientists and engineers, linear system theory using a state space approach along with its many applicable matrix computation capabilities can provide a desirable high potential foundation.

System Engineering Methodology

Engineering approaches to complex system analysis can begin by assuming a linear polynomial behavior representational state space model; however, review of some biology modeling literature suggests that CICD should begin with a nonlinear polynomial representation. To this end, CICD can use a representation that yields numerical results that are accurate to second order (bilinear) numerical accuracy. If high order contributions are found to be required for specific studies, CICD software and systems can be structured to accommodate such requirements. Such software and systems can include any of a variety of steps, such as the observation that unknown model coefficients appear linearly in each of the nonlinear polynomial terms. This can allow an elementary rearrangement of the polynomial terms whereby the linear unknowns are uniquely extracted. Such a step can produce an n×1 vector of unknown coefficients and a matrix that captures all possible nonlinear effects. The resulting {matrix}×{vector} equation can be in standard linear state space matrix computation form. Applying standard signal processing algorithms to this problem specification form can reveal biologically important system behaviors.

Because CICD can be used to model the actual immune system behaviors from observations, few if any immune sub-system behaviors can be ignored and all nonlinear coupling interactions can become observable. No analyst-imposed simplifications may impact the data extraction process. CICD can see everything that happens, with second order accuracy via the patient biomarker data used to quantify modeling approximants.

Overview of CICD's Analysis Process

Figure 13:
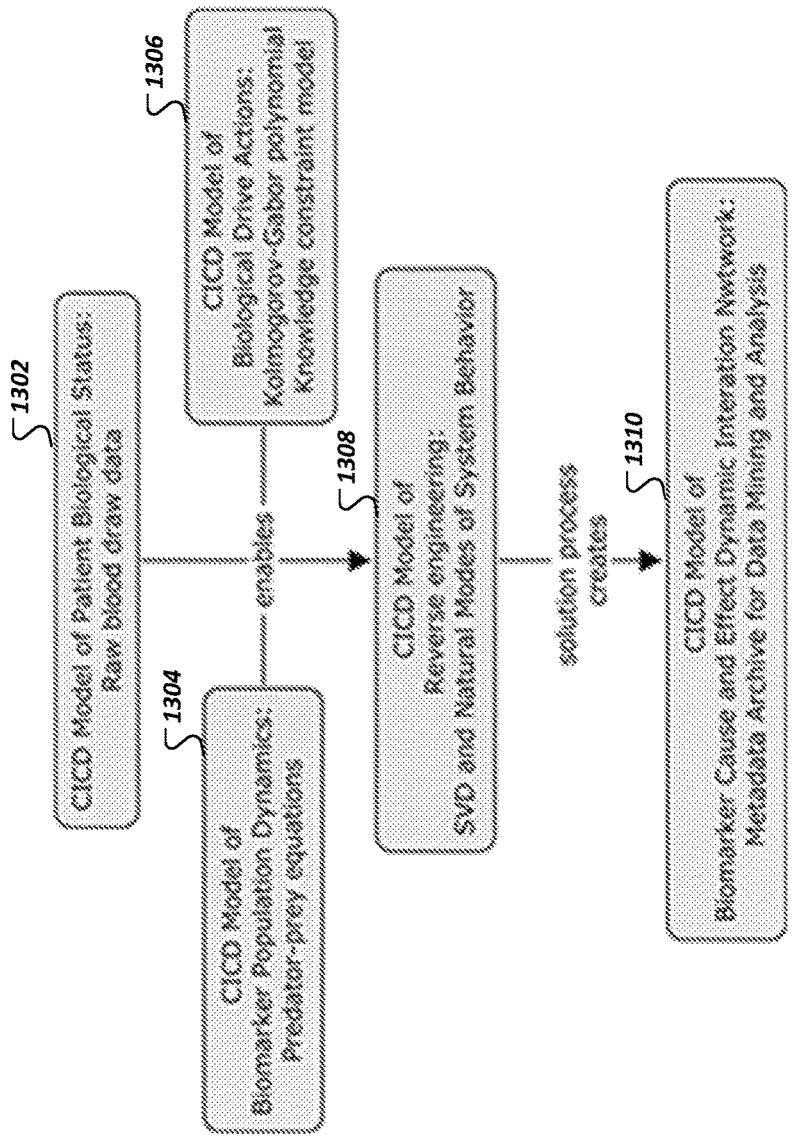
FIG. 13 is a flowchart of an example data modeling technique that provides an analysis process framework.

FIG. 13 is a flowchart of an example data modeling technique 1300 that provides an analysis process framework. The example technique 1300 can be similar to and used in combination with the example technique 100 described above with regard to FIG. 1. The technique 1300 can include data flow linkages from data collections and model creation steps used for data processing, to the dynamics characterization database creation and data mining steps. The example technique 1300 can be performed by any of a variety of appropriate computer systems, such as a system including one or more computing devices (e.g., server, client computing device, desktop computer, laptop, mobile computing device). For example, the technique 1300 can be performed by a computer server system with one or more computer servers that are programmed to execute the technique 1300, such as a distributed server system (e.g., cloud-based computer system). Such an example computer system for performing the technique 1300 can be, for instance, a CICD system, which is described in this document to illustrate the disclosed computer-based technology. Computer systems and/or computing devices other than the CICD can also be used to implement and/or perform the technique 1300 and other aspects of the computer-based technology described throughout this document.

The technique 1300 depicts different components of the CICD's architecture and interactions between the components. The model based system identification technique 1300 can begin with serially collected peripheral blood biomarker data records and the selection of a biomarker set that identifies CICD analysis focus (1302). The mathematical modeling process begins with a set of non-linear predator-prey matrix equations generalized to deal with any number of biomarkers classified as either cytokine or cell (1304). The example equations 1304 can include some and/or all possible cause & effect interactions identifiable from well-established biological knowledge and experience.

The technique 1300 can join three biology-based math models (1302-1306) to create a system math model for reverse engineering cause and effect dynamics (1308). A modal analysis solution portion of the technique 1300 can create an archive of information used for characterizing patient and multi-patient cause and effect network interaction dynamics.

Reverse Engineering Model Development

Reverse engineering (1308) in the example technique 1300 can work by measuring observable states (i.e., processed blood products), and using these variables to describe a dynamics model for analyzing interaction effects. Conventionally, rigorous mathematical model did not exist to provide a natural law foundation for CICD. Instead, one can only observe the response of the immune system indirectly through analyzing the components of patient processed blood samples, CICD self-constructs a model by invoking reverse engineering analysis methods. Reverse engineering (1308) works by defining an approximant linear (straight line) model for connecting biomarker data measured at successive data sampling instances. With this, a time record for all drive actions can be computed for the input data record's chain of data sampling time intervals. The reverse engineering model (1308), to be discussed, consists of model-based system equations expressed by a Kolmogorov-Gabor matrix post processed by a Singular Value Decomposition (SVD) linear algebra technique (1306). Results quantify a time record of the least effort set of drive actions required to re-generate CICD input data as specified by patient biomarker blood draw measures. The SVD generated least effort solution can provide a computational realization of the system actions that collectively cause biomarker population change. Model-based system dynamics characterization information can then be archived using a sparse data format within the CICD database for efficient data mining and insight extraction (1310).

CICD Model of Patient Biological Status: Raw Biomarker Data (1302)

CICD analysis can begin, for example, with a model for cancer immune control dynamics for a specific patient over a 2-week test period (example of 1302). The example model for biology, as observed, consists of a defined set of biomarkers. Set membership is assumed to be representative of the CICD analysis objective. The biology model used in this example includes 24 cytokines: FRACTALKINE, GM-CSF, IFNa2, IFNg, IL-1b, IL-1ra, IL-2, IL-4, IL-5, IL-6, IL-7, IL-8, IL-9, IL-10, IL-12p40, IL-12p70, IP-10, MCP-1, MCP-3. MIP-1a, MIP-1b, TNFa, TNFb, VEGF and 7 cell phenotypes: CD3, CD3.4, CD3.8, CD16.56, CD3.69, CD4.294(Th2), CD4.TIM3(Th1). Data records contain, 10 blood-draw data samples taken over a 2-week period for 22 patients with metastatic melanoma, not on active therapy (Table to describe patient population). These records display biomarker population size and change. During analysis of cancer patient data, the need for a healthy patient data study became apparent. 15 healthy, cancer-free volunteers were obtained and peripheral blood was collected and raw biomarker data acquired according to the same cancer patient protocol. Completed cytokine data has been obtained and preliminary profiling analysis has begun.

Biomarker drive actions are, for example, reverse engineered and analyzed for clinically relevant cause and effect insight (1308). This can include a complementary model for biomarker value transitioning between sequential data sample values. It is valid and common engineering analysis practice to assume and apply a linear interpolation approximant (straight line) model, as well as other models. With this, drive action records can be computed for the time intervals between all test period data sampling points. Based upon the assumption that obtaining biomarker blood data is a noise-free measurement process. CICD can then, for example, use a fully deterministic input data set with reverse engineering results auto-checked to insure that normalized computational error measures are less than 10-10.

Although not normally utilized, normalized mean value biomarker can measure per patient provide a profiling capability to group and rank order patients and biomarkers before any CICD analysis work begins. Two example biomarker sets are defined: all cells, all cytokines. Then biomarker record mean values are computed for each set member. The maximum value per set can be identified and used to normalize respective set members. These can be, for example, the normalized average values for all biomarkers used for test period reverse engineering computation. Together they can quantify each patient's test period biomarker interaction dynamics cause & effect operational environment (i.e., system test period biomarker availabilities).

CICD Model of Biomarker Population Dynamics: Predator-Prey Equations (1304)

CICD can use a systems-engineering approach with no simplifications imposed. A major design goal for CICD has been to identify, quantify, and characterize the underlying networks of connectivity that couple the internal behaviors of the homeostasis and immune regulatory (IR) system. The development process for CICD begins by building on the success of modeling strategies for physical systems. For modern engineering applications, the cornerstone for real-world application can be the development of finite element modeling capabilities, which can allow solutions to be expressed as a sum of normalized displacement shapes and associated frequencies obtained, for example, via eigen-analysis. Models can be validated by: exciting the system, observing response, and comparing measurements to computed predictions of behavior, CICD can mirror this process.

Early in CICD's development process, it was recognized that biology concepts do not correlate well to the mechanical system concepts of mass, elasticity, damping and Newtonian dynamics. Immune system dynamics behaviors are better described in terms of interacting biomarker population dynamics. Hence CICD can use, for example, a generalization of the Lotka-Volterra predator-prey equations (example of 1304). Such generalization of the predator-prey paradigm for high dimension systems can allows some or all biologically possible nonlinear coupling effects to be approximated. CICD builds a set of first order non-linear differential equations. The position and velocity state variables common in engineering dynamics may not be used. CICD state variables can be measures of biomarker (predator (cell)), prey (cytokine)) population size. CICD's power can come about by organizing analysis equations in a format consistent with the methods of linear analysis matrix decomposition. This enables the discovery of time varying predator-prey natural modes of behavior: including all associated interactions and cross couplings. Recovered interaction models characterize, in a normalized manner, all internal biomarker networks that are potential targets for therapeutic interventions.

CICD Model of Biological Drive Actions: Kolmogorov Gabor Polynomial (1306)

To specify all predator-prey population impacting drive actions CICD can use a generic polynomial format that enables all non-linear homeostasis and IR function enabling drive actions to be approximated without a need to define and estimate an uncountable number of non-linear drive action expressions and associated parameters. The core math engine for CICD can be, for example, the Kolmogorov-Gabor polynomial for which every element of the polynomial has a biological interpretation (example of 1306). Because the Kolmogorov Gabor polynomial is so general in its modeling capabilities, CICD can define a constraint knowledge model that pre-defines which polynomial math elements are biologically real. Only data for biologically real variables may be retained in the model. For example, the fact that cytokines do not produce cells or receptors can be specified to the model and then rigorously enforced in the system characterization matrix creation process. The benefit is that non-physical results can be eliminated from the solution process. A significant additional benefit of the constrained polynomial solution strategy is that the size of the matrix processed becomes much smaller. This reduces computational effort and improves the solution accuracy at the same time.

CICD development began with the vision that a whole system model should begin with many biomarkers (to insure that nothing will be missed); then as insight evolves, justifiably smaller models would emerge. Capability development efforts have typically used a network of 10's of dynamically interacting biomarkers and 1000's of drive action elements. For problems of this scale a framework for information organization and recovery is essential. Relative to FIG. 13 this framework joins the biological models of raw blood draw data, dynamic constraint modeling and predator-prey modeling. The visually complex but easy to apply Kolmogorov-Gabor polynomial services this need; namely:

$$Y(x_1, \ldots, x_n) = a_0 + \sum_{i=1}^{n} a_i x_i + \sum_{i=1}^{n} \sum_{j=i}^{n} a_{ij} x_i x_j + \sum_{i=1}^{n} \sum_{j=i}^{n} \sum_{k=j}^{n} a_{ijk} x_i x_j x_k + \ldots$$

Each variable of state $x_1, \ldots, x_n$ in the Kolmogorov-Gabor polynomial represents an element of the biomarker population. The left equation side symbol $Y(x_1, \ldots, x_n)$ approximates the resultant of all drive action elements acting on one system biomarker. The right side of the equation aggregates all possible elements of drive action, where the unknowns are parameters that respectively multiply each of the model's constant, linear and nonlinear biomarker product terms. For example, if the system model is of dimension n, the system model will have exactly n biomarker equations and n such $Y(x_1, \ldots, x_n)$ action resultants. The parameters $a_0, a_i, a_{ij}, a_{ijk}, \ldots$ are reverse engineering unknowns. CICD's constrained Kolmogorov-Gabor polynomial framework links the math model to knowledge of all biologically possible biomarker interactions to yield meaningful computational results insight.

CICD Model of Reverse Engineering and Constraint Knowledge (1308)

A variety of models can be used, such as 2nd order Kolmogorov-Gabor polynomial models. This can imply, for example, that CICD's predator-prey framework elements of drive action are modeled as linear and bi-linear state product terms with each having one unknown coefficient. The tumor microenvironment can be modeled as a system of cytokines and cells with receptors for both cells and cytokines observable by blood draw and interacting as cell predators and cytokine prey. Bonding of ligands to receptors can create a measurable cellular response as the result of, at this level, unspecified internal cellular signaling (neural) pathways. Every cell receptor-ligand bonding triggers a cellular pathway to a specified IR control command that can be modeled, for example, either as an element of linear drive action or a bi-linear drive action. The knowledge model employed, views each drive action element as having a target biomarker that has its population impacted by a source biomarker that has its action strength impacted by a modulator biomarker. Cells can be viewed as having 5 possible basic responses to a drive action; namely: 1, 2—create new cells and cytokines, 3, 4—create new receptors for cells and cytokines and 5—chemotaxis. The knowledge model when quantified with cell and cytokine identifiers can enable a simple algorithm to identify all unknown parameters with potentially non-zero value. The 4 biomarker and receptor creation actions that act on both cell and cytokine biomarkers can be modeled by bi-linear Kolmogorov polynomial terms while chemotaxis action that acts on cell biomarkers can be modeled by linear Kolmogorov polynomial terms.

The knowledge model can create a system-viewing filter realized by the SVD. Through this filter only biologically possible input-output and internal biomarker coupling relationships are identifiable. The model implicitly recognizes that biomarker data records can contain information of unknown origin, unrelated to the system's CICD viewing filter, for example all that is associated with the function of body organs. Also implicit within this representation model is the inclusion of actions that support system homeostasis. It is the knowledge model that enables problem size reduction and auto-enables insight-yielding information trace back to root target, source and modulator biomarkers; while also allowing measured observations to quantify a variety of dynamic interaction strength measures. Relative to FIG. 15 all of this work can enable CICD to specify math model detail so as to form the systems dynamics characterization matrix used for the reverse engineering.

CICD Model of Natural Modes of System Behavior (1308)

CICD's Kolmogorov-based framework can yield, for example, a system of first order differential equations expressed, at each time instant, as a linear relationship between a relatively short vector of biomarker population rate of change variables and a very long vector of Kolmogorov-Gabor polynomial unknowns. Connecting these effect & cause vectors is a long thin rectangular matrix. It can contain biomarker (linear) and biomarker product (bi-linear) values. It can have one non-zero value per column, auto-arranged by knowledge model specification. This quantifies CICD's system (reverse engineered) characterization matrix. Three Kolmogorov matrices can be created; namely: one for just linear terms, a second for just bi-linear terms and a third containing both linear and bi-linear terms so as to model the complete non-linear predator-prey problem. The standalone linear and bi-linear matrices can be used only for drive action detail investigations and not discussed further herein.

Before applying SVD; it is noted that, in the equation below, the invertible cause (a) and effect {dx/dt} matrix relationship solution can have infinitely many solutions. To obtain a unique solution SVD recovers the solution that is characterized by a minimal change or norm. The resulting minimal change, Moore-Penrose pseudo-inverse, solution can be consistent with nature selecting a minimal effort solution for its biologically constrained biomarker response, to a large distribution of drive actions. Homeostasis drive action realization can be entirely consistent with the principle of least effort; i.e., it is reasonable to speculate that evolution preferentially selects a response behavior using minimum resources and energy. This SVD property provides CICD with an implicit homeostasis dynamics modeling capability.

Symbolically, the CICD dynamics analysis relationship can be expressed in matrix form as:

$$\left\{\frac{dx}{dt}\right\} = [K]\{a\} = [U][\Sigma][V]^T\{a\}$$

Herein, x's are biomarker variables of state, a's unknowns and K's one of the 3 Kolmogorov matrices, the second equality sign introduces the SVD relationship that equates matrix [K] to the matrix product of (Left Singular Vectors) LSV's in [U], singular values in [Σ] and (Right Singular Vectors) RSV's in [V]T. The atypical step of embedding all non-linear variables of state within the matrix [K] makes this matrix quantifiable. The computationally step is exact and it transforms the previously intractable non-linear predator-prey dynamics problem into a classic linear matrix algebra problem. This step mirrors how engineering analysis uses operational calculus and Laplace transform theory to map a system of linear time domain differential equations into a system of linear frequency domain algebra equations for control system stability and performance study.

The SVD algorithm can generate LSV's and RSV's that are orthogonal along with singular values that act as scale factors. Mirroring engineering analysis, CICD refers to each column of the LSV array [U] as a system mode of natural behavior. Since these LSV's are orthogonal it follows that $$[U]^T\left\{\frac{dx}{dt}\right\} = [\Sigma][V]^T\{a\}$$

The standard modal analysis operation of pre-multiplying both equation sides by [U]T transforms the set of fully coupled equations into a set of n decoupled generalized modal equations. The decomposition can lead to views into the relative strengths of all biomarker Interactions as a time function, independent of all values contained within the vectors of cause unknowns (a) & effect {dx/dt}). Unlike mechanical system linear vibration analysis, biological systems are governed by non-linear predator prey relationships and the system equations are time varying. CICD resolves this problem, for example, by repeating the SVD modal analysis operation at every time instant for all patients. Associated time history records provide the least effort system characterizations required to reversibly link population cause {a} drive action unknowns to biomarker population effect {dx/dt} rate of change data.

By decomposing the matrix model using the SVD method at every time step, CICD recovers a time history dynamics characterization model for biomarker interaction networking and behavior. The LSVs can define a set of unique time varying orthogonal natural behavior functions. The RSVs cam define dynamic relationships between system unknowns and natural behavior drive actions while the singular values are associated scale factors. Dynamics characterization information can be embedded within LSV & RSV time records along with all metadata used to trace every element of drive action back to an observed biomarker state value for system behavior insight creation.

Results: Patient Peripheral Blood Derived Serial Biomarker Data (1310)

Patient peripheral blood immune biomarker data records can provide input data for CICD analysis along with a means to test period profile each patient for protocol patient grouping and rank ordering. Analysis builds upon the assumption that data sampling is of a continuous biomarker population change process with rate of change measures equating to the sum of all change impacting drive actions. CICD can be designed to support the ability to create one large order systems analysis model to base all patient reverse engineer results upon. The objective is to compare CICD analysis results from many patients relative to their profiling measures, computed directly from patient raw blood draw biomarker data. Biomarker data records can be non-linear oscillatory and provide all CICD reverse engineering input data.

Figure 14:
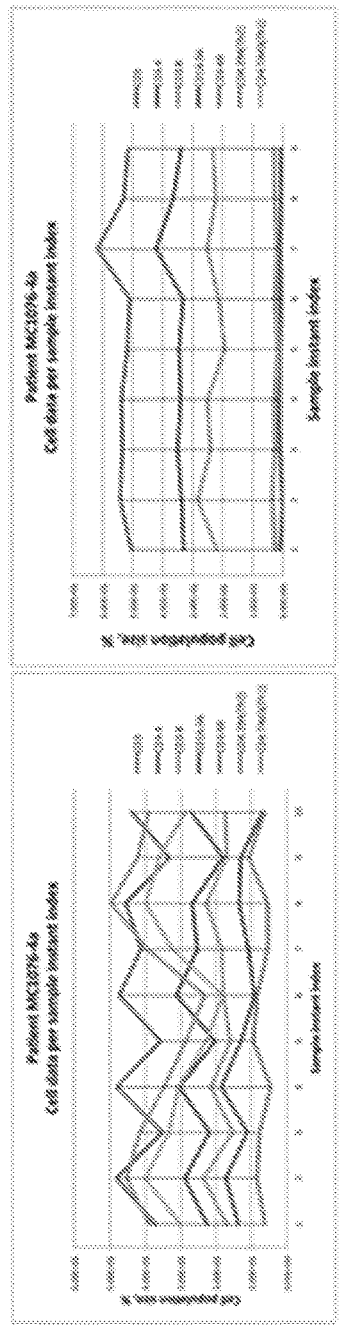
FIG. 14 illustrates an example linear interpolation model used for biomarker population value transitioning between sample instances and how cell data records vary significantly across patients.

FIG. 14 illustrates an example linear interpolation model used for biomarker population value transitioning between sample instances and how cell data records vary significantly across patients. In FIG. 14, the 7 cell population values for example patient MC1076-4 have significant value; while only 3 of the 7 cell values for example patients MC1076-16 have significant value. The inference, from the perspective of enabling homeostasis and IR function is that patient MC1076-16 is severely cell resource handicapped with respect to cellular drive action execution.

FIG. 14 depicts example cell population size values per sample instant index, seven cells and two patients, including 1) test period records are oscillatory, 2) mean values (not shown) are sufficiently well defined for quantifying test period profiles, 3) patient cell mean values vary significantly, 4) highlights need for patient test period profiling to characterize test period system resource availabilities.

Figure 15:
FIG. 15 illustrates example normalized patient test period cell-profiling measures sorted relative to value.
Figure 15:
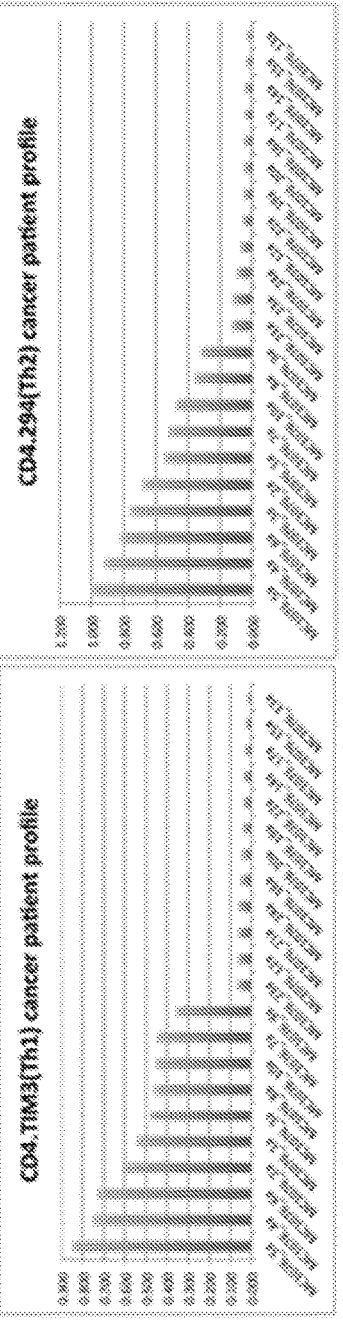

FIG. 15 illustrates example normalized patient test period cell-profiling measures sorted relative to value. These quantify the patient's test period environment in which all cause & effect relationships are realized, observed and reverse engineered. Analogous profiles are generated for all other cells and cytokines. The example results show that across the patients, profiling measures support patient grouping and rank ordering and that patient test period profiling is an essential element of the CICD results interpretation process. Although the number of cancer patients available is small: the graph for CD3.8 illustrates patient rank ordering, CD16.56 illustrates identification of patients having very high vs. very low population value measures, CD4.TIM3 (Th1) illustrates patient grouping relative to low vs. high raw data mean values, and CD4.292(Th2) illustrates grouping with rank ordering. The ability to link CICD results to patient cellular drive action profiles is used to compare patients and patient groups with similar and dissimilar state test period system resource availabilities and to link reverse engineered drive action records to input data records.

Average cytokine profiling can be used measure across cancer-free and cancer patients for computing Cancer-free minus Cancer (CF-C) biomarker differences. These results are summarized in FIG. 16. Therein column 1 lists cytokine names, columns (2, 3) contains (cancer-free, cancer) patient profiling measures, column 4 contains the algebraic difference normalized to a max 100.0 scale and column 5 provides a strength characterization label.

FIG. 16 depicts example cancer free vs. cancer patient average cytokine biomarker profiling measures. Lists cancer free and cancer profile measures averaged across respective groups. CF-C is the difference normalized to a maximum value 100.0. Strength label bounds, judged to be of CICD clinical decision-making value, are set at 1.0 and 10.0.

CICD Analysis of SVD Results: Natural Behaviors, Dominators and Supporters

For example, at every time instant step 32 orthonormal linearly independent LSV's can be computed per patient via SVD. Mirroring the semantics of modal analysis each LSV can be referred to as a natural behavior (NB). Associated identification of a dominator biomarker for each NB and supporters of significance uses LSV biomarker element value squared; this value can define each biomarker's percent participation within the NB. Identification can be based on a 7.5% threshold value. It creates a participation significance window. The selection of 7.5% is a CICD min-max decision-making problem. The selected threshold value enables a unique system biomarker "dominator" nametag to be assigned per NB and all supporters of significance to be listed.

The CICD process can reverse engineer drive actions that produce effects observed between successive data sampling instances. It can do this by taking interpolation steps along straight-line segments used to model for how biomarker values transition between serially collected data sampling points. Step size selection is another CICD min-max problem; testing has shown that 6 interpolation steps works well; i.e., it minimizes computational burden while maximizing computationally derived insight value. Resultant per patient matrix maps of biomarker supporters per NB dominator model show mean value occurrence detection counts and resultant mean value participation values across full patient time records. Per patient maps can be generated and archived in the CICD database with computed values uniformly normalized to a 42 data sample 7-day week period.

Figure 17:
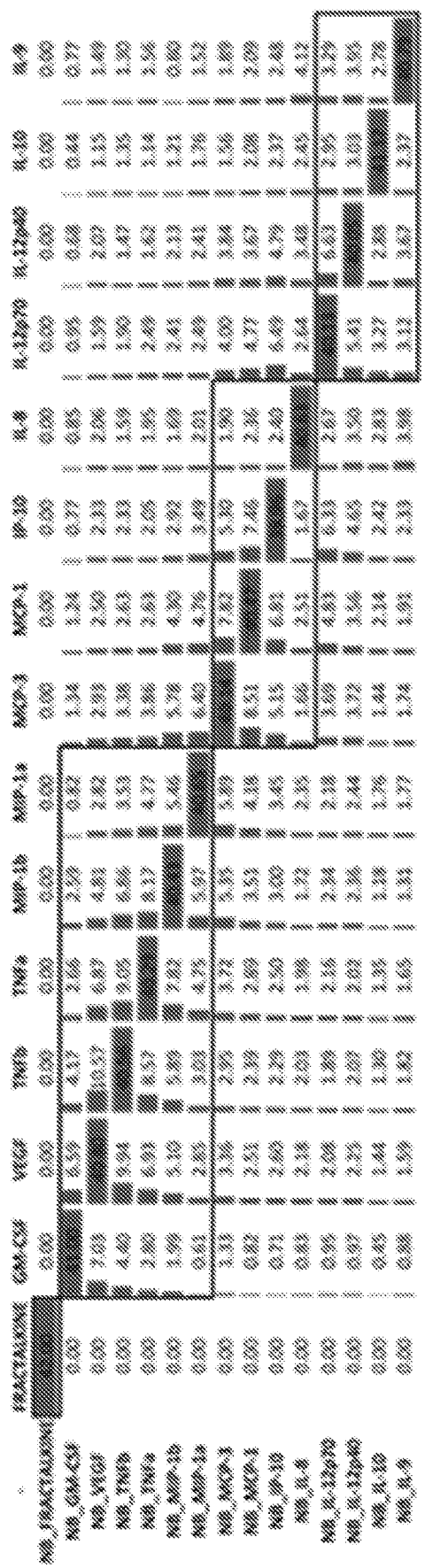
FIG. 17 depicts an example matrix map of biomarker support occurrence counts for several natural behavior (NB) dominator modes.

From a mathematical perspective, the CICD problem has 1000's of cell-cytokine dynamic constraint relationships that are possible, with only a small number of biomarkers available to satisfy all. Dominator-supporter relationships identify biomarker sets and pairs that are concurrently used most frequently by the system to satisfy all knowledge model inferred constraints with least effort at every time instant. FIG. 17 shows example mean value occurrence detection counts averaged across all patients. Rows are biomarker named (natural behaviors) NB's. Columns are biomarkers. Diagonal blocks boxed by bold lines partition the matrix. Associated biomarker sequencing exposes relative strength grouping patterns that emerge when all patients and all time data is aggregated. These groupings are associated with all patient functional purpose viewing. Aggregated reverse engineering LSV data reveals that these are the functions most frequently executed across all protocol patient time records. From the perspective of system engineering this LSV matrix blocking process decomposes the system into sub-functions that can be visualized as stand-alone system functional action enablers that interface with others sub-functions. Analysts must provide biological meaning to each.

Even though FIG. 17's auto-blocking process has a subjective component and patients are few, Melanoma cancer patient data shows that biologically meaningful groupings emerge. Values within diagonal blocks quantify the degree to which associated sub-function biomarkers interact as concurrently acting dominator-supporter pairings while off diagonal terms quantify interaction strength between sub-functions.

FIG. 17 depicts an example matrix map of biomarker support occurrence counts for several natural behavior (NB) dominator modes. Counts are averaged across all patients and normalize to a 42 data sample 7-day week. Rows identify NB dominator modes, columns identify biomarker supporters, ordering provides the mathematics to biology linkage needed to expose both sub-functions and dynamic coupling. FIG. 16's cancer-free vs. cancer patient data identifies biomarkers with highest CF-C cancer sensitivity value. Correlations pinpoint sub-functions most sensitive to cancer's impact.

Several example insights emerge from FIG. 17 that can be linked to the cancer-free vs. cancer difference data in FIG. 16 that quantifies each biomarker's behavioral sensitivity to Melanoma cancer; such as:

Three sub-function blocks of significance exist; namely:
(GM-CSF, VEGF, TNFb, TNFa, MIP-1a, MIP-1b) Within this block cytokines (VEGF, TNFb) have cancer sensitivity measures (30.441, 11.908) resp.
(MCP-3, MCP-1 IP-10 and IL-8)—Within this block cytokines (MCP-3, IP-10, 11-8) have cancer sensitivity measures (17.494, −7.991, −13.150) resp.
(IL-12p70, IL-12p40, IL-10, IL-9)—Within this block cytokine IL-12p40 has cancer has the sensitivity measure (2.585)
Cytokines not listed above all have weak cancer sensitivity measures
Sub-function coupling cytokines MCP-3 and IP-10 have strong cancer sensitivity measures (17.494, −7.991) resp. These cytokines quantify sub-function couplings that have Melanoma cancer sensitivity.
When cancer-free patient cell data is made available cancer-free vs. cancer patient results will be more fully generated, quantified and compared.
FIG. 15 profiling results; such as provided for CD16.56 and CD4.TIM3(Th1), infer that groupings other than "all" will lead to more focused IR sub-function based biomarker pairings and insights into cancer behavioral impact.

CICD Analysis of SVD Results: Drive Action Time History Records

The analysis power of the modal analysis method can rest in its ability to fully decompose a complex system dynamics model for n interacting variables of state into exactly n linearly independent generalized modal coordinate models. LSVs connect generalized coordinates to what is observed; namely biomarker population size variables. RSVs connect generalized coordinate drive to the sum of all biomarker population change causes. RSVs have one modal element associated with each unknown in the CICD dynamics analysis relationship. The unknowns each relate to specific Kolmogorov polynomial elements of drive action specification. These all vary in value between +1.0 & −1.0 across the patient's test period. When graphed, views are obtained into the decoupled system time history of every element of drive action.

Within this modal analysis framework, CICD can create a time record representation of the least effort pathway taken by homeostasis and IR control action as it reverse engineers a representation of the population change drive action that tracks input as specified by the transition function that chain connects sequential blood draw instances. This usage of an approximant to compute an approximate system dynamics characterization mimics methods, such as Rayleigh's principle, extensively applied in structural engineering before the discovery of linear matrix decomposition methods and the advent of digital computation.

Figure 18:
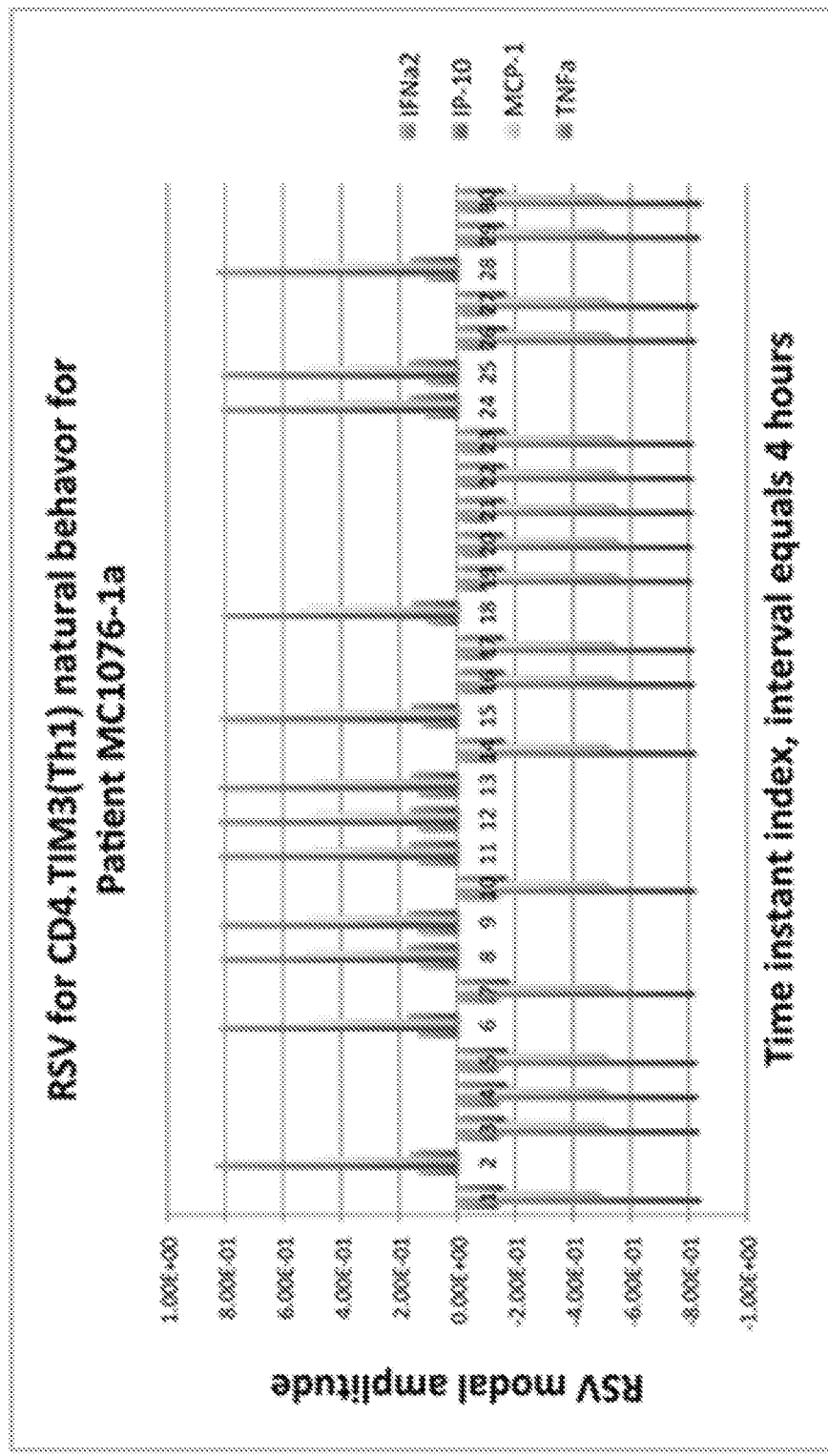
FIG. 18 depicts an example patient time instant RSV records for modulated Th1 T-helper cell natural behavior drive action components.

To illustrate this, an example patient MC1076-1a drive actions associated with the cytokine modulators that contribute 99% of the modal drive action acting on the CD4.TIM3(Th1) dominated NB are presented in FIG. 18. The knowledge model identifies that the RSV associated with this NB_CD4.TIM3(Th1) has significant cytokine modulators IFNa2, IP-10, MCP-1 and TNFa. It is important to note that these modulators of drive action act concurrently together over the test period segment shown with very slight amplitude variation. Furthermore from the data in FIG. 16 these modulators have CF-C cancer sensitivity profile measures (2.172, −7.991, 1.509, −1.100) respectively. Together this information set identifies that for patient MC1076-1a, the prime modulators are IP-10 and MCP-1 for CD4.TIM3 (Th1) drive action execution, that IP-10 is the strongest and that it has the highest cancer sensitivity measure.

This illustration is prototypical of all patient time records (1,000's) and prototypical of the output of a digital sample data control system. Results are a reflection of the SVD's ability to accurately compute whole system least effort solutions with normalized computational error less than 10-10. From the perspective of sampled data control design one is immediately drawn to suspect that IP-10 is, for this patient and natural mode of behavior, key to understanding the IR systems reaction to cancer invasion.

FIG. 18 depicts an example patient MC1076-1 time instant RSV records for modulated Th1 T-helper cell natural behavior drive action components. Drive action pattern is prototypical of classic sampled data control action. Modal amplitude values squared can define relative strength of participation. At each time instant 99% of CD4.TIM3(Th1)'s NB modal drive action is defined by the concurrent action of modulators (IFNa2, IP-10, MCP1, TNFa). IP-10 is the strongest and has the highest figure #4 cancer sensitivity measure.

CICD Analysis of SVD Results: Modulators of Cellular Source Driven Action

Linear drive actions can have source without modulation. These drive actions model unrestricted source stimulated biomarker target population growth or decay, i.e., chemotaxis recruitment, purging, and cytotoxicity. Bi-linear drive actions can have a modulated cell source that stimulates a biomarker target population, these model homeostasis maintenance, resource limitation constraints, IR control action commanding and autocrine signaling.

The degree to which specific cytokines most strongly impact both linear and bi-linear drive actions acting on cytokine and cell dominator NB's of all patients can be discovered first. The intent is to discover which cytokines dominate drive action activity and which have significant relationships with (CF-C) biomarker cancer sensitivity as shown in FIG. 16.

Figure 19A:
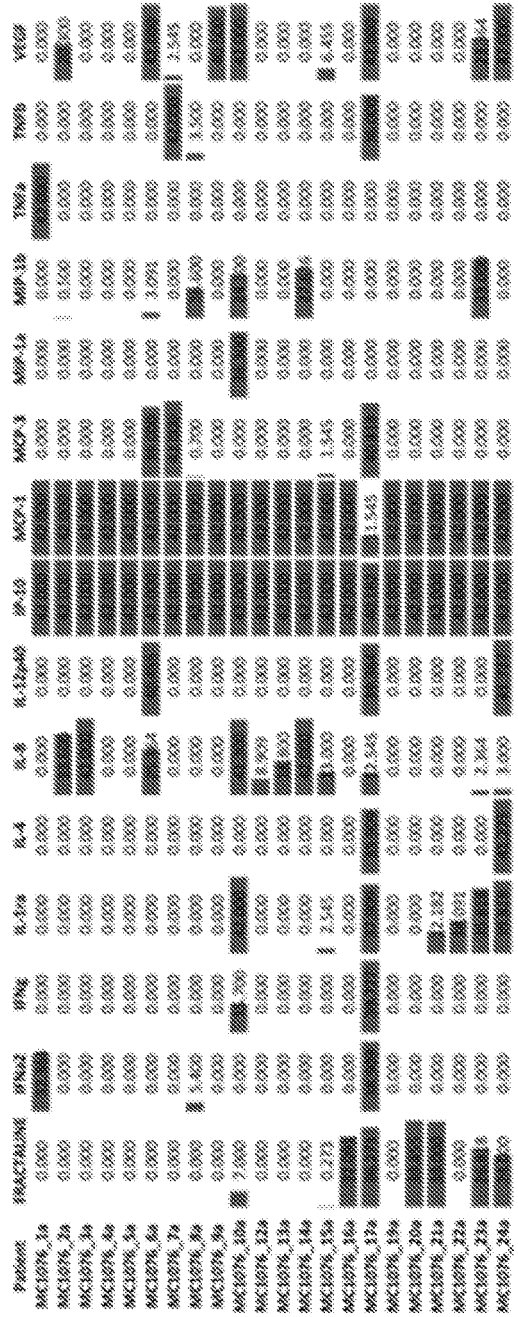
FIGS. 19A-B depict example patient test period RSV modal elements counts for drive action instances.
Figure 19B:
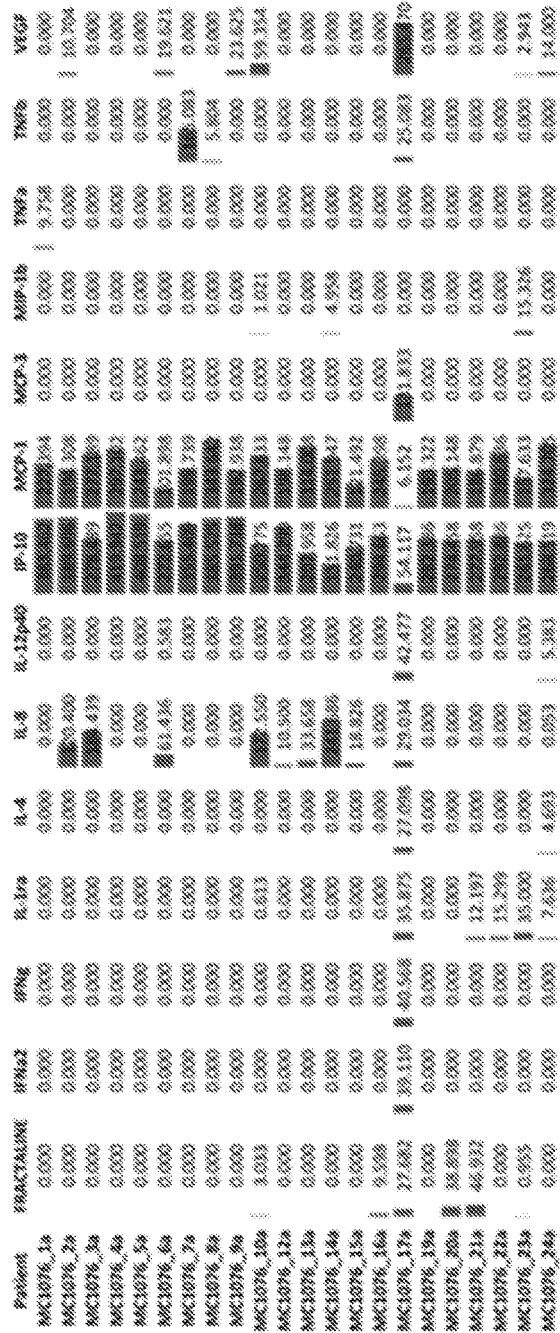

Cell dominator NB's can have cell targets impacted by linear cytokine and bi-linear cellular autocrine signaling drive action sources. The modeling of paracrine drive action is feasible; but not included in this study. The linear drive action list can have 100's of elements per time instant while the bilinear drive action list has 1000's of elements per time instant. As illustrated in FIG. 18, RSV modal value can model one element of drive action at a time instant. With 1000's of such modal amplitude records it is computationally expedient to use a threshold measure to identify only drive actions of significance. RSV element value squared (i.e., modal participation value) greater than 1.0% of the max drive action participation value is identified to be significant. Selection of 1.0% is another CICD min-max decision making problem. FIGS. 19A-B respectively show example occurrence detection count tables for linear and bi-linear drive action cases. Occurrence detection counts can be obtained by summing all patient drive action detections of significance acting on all patient system NB's. FIGS. 19A-B respectively quantify the relative degree to: a) which specific cytokines stimulate all linear cellular drive action, and b) which specific cytokine modulators impact all bi-linear drive action. Table rows can be associated with specific patients while columns are associated with drive action associated cytokines. Count values can be normalized to counts per 42 data sample 7-day week. FIGS. 19A-B clearly show that cytokines IP-10 and MCP-1 dominate all patient linear and bi-linear drive action with the marginal exception of patient MC1076-17a. Shown also in these example figures are many other biomarker columns with significant (green bar) value. Most are associated with cytokines that stimulate linear drive action. Only cytokine IL-8 and to a lesser degree TNFb and VEGF have significant green value bars for both linear and bi-linear drive actions. Referring to FIG. 16 biomarker cancer sensitivity measures, it is noted in FIGS. 19A-B biomarker columns correlate with FIG. 16 biomarkers labeled strong or significant. The most plausible explanation for the high value data elements in FIG. 19A-B is that these are pointing directly to patient specific biomarkers responding to Melanoma cancer stimulated behavior. Furthermore it is the linear component of drive action that has the largest number of biomarkers with large value and high cancer sensitivity measure.

FIGS. 19A-B depict example patient test period RSV modal elements counts for drive action instances with greater that 1% participation strength, normalized to counts per 42 data sample 7 day week. Cytokines with zero counts are not shown. Rows identify patients. Columns identify cytokine biomarkers. IP-10 & MCP-1 are of dominating importance in both figures. Other cytokines listed having significant occurrence count values consistently align with FIG. 16 table biomarkers having significant Melanoma cancer sensitivity. Results are pointing to follow-on CICD analysis work; i.e., directly to specific biomarkers, patients and FIG. 17 identified sub-functions with cancer impact sensitivity.

FIG. 19A depicts example linear drive action cytokine stimulation count usage map. These drive action components are associated with chemotaxis recruitment, purging and cytotoxicity.

FIG. 19B depicts example bi-linear drive action cytokine modulated cell stimulation count usage map. These drive action components are associated with homeostasis maintenance, resource limitation constraints, IR control action commanding and autocrine signaling.

Figure 20:
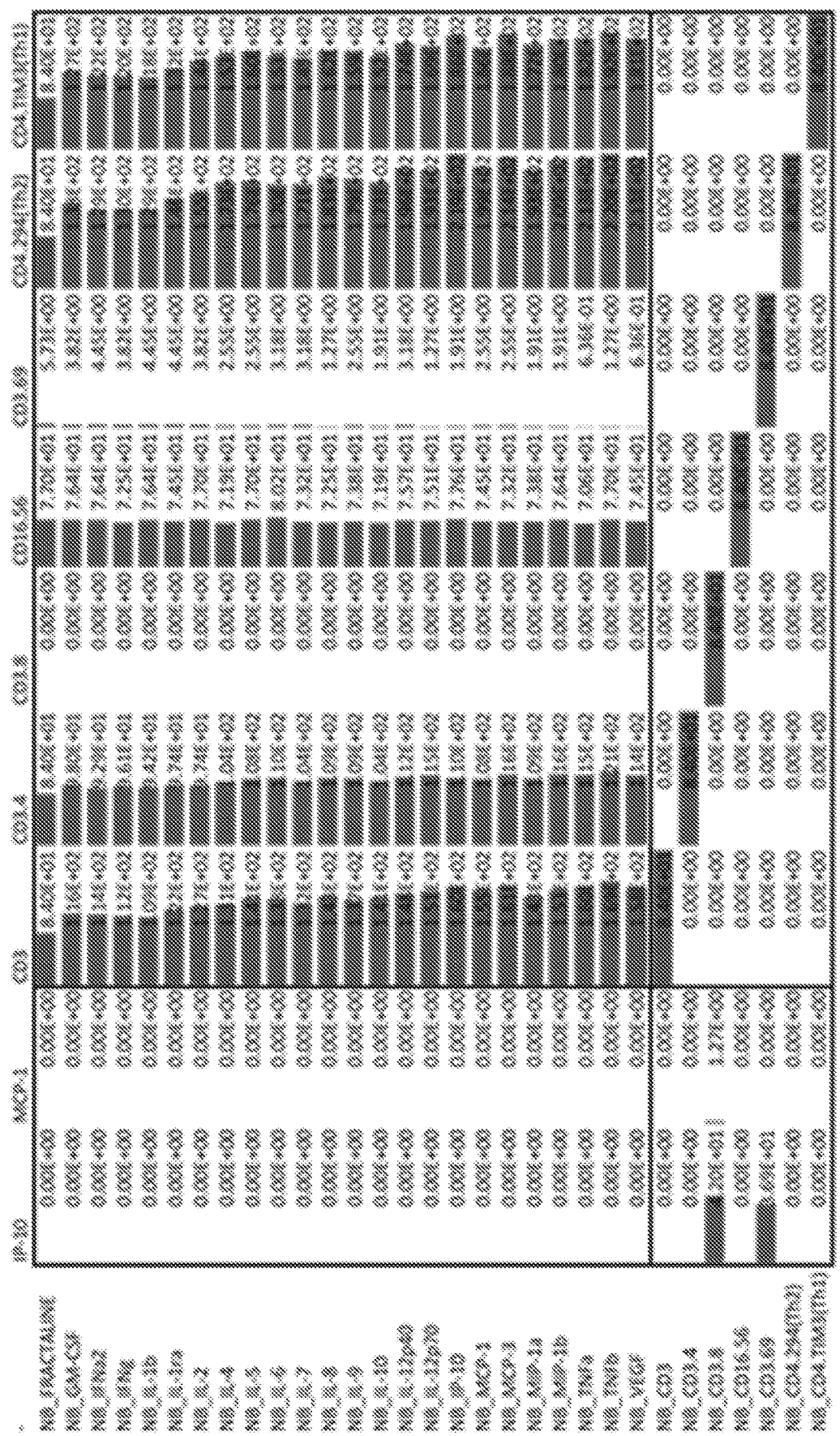
FIG. 20 illustrates an example inverse of FIGS. 19A-B.

Reverse Engineering: Linear & Bi-Linear Sources for Natural Behavior Drive Action FIGS. 19A-B are focused on quantifying the resultant role of specific cytokines acting as the source of linear drive action or as the modulator of cell initiated drive action acting on all patients and all biomarker dominated natural behaviors. FIG. 20 illustrates an example inverse of FIGS. 19A-B that can be quantified for each patient. It quantifies the resultant role of specific cells acting as the source of drive action acting on a specific patient and its set of biomarker dominated natural behaviors. To illustrate this ability, all per patient resultant cell and cytokine strength measures underlying the drive actions shown in FIGS. 19A-B are computed. To illustrate the process, FIG. 20 provides an example matrix map that organizes resultant source drive action data for patient MC1076-5a. Rows identify specific biomarker NBs, columns identify specific biomarker drive action sources. Values are normalized occurrence count measures for all biomarker sources associated with least effort drive actions. One such matrix map can be generated per patient; zero valued columns are not shown, bold lines partition cell & cytokine associated information and all information is archived in the CICD database in a sparse matrix format compatible with data mining and follow-on analysis needs.

The bottom left (NB_cell, cytokine) partition provides example patient specific detail underlying FIG. 19A. Values shown are normalized counts for all cytokine source linear drive actions acting on the row identified cell dominated NB. This models cytokine induced cellular chemotaxis, recruitment and purging. Across patients, this partition shows considerable variability. The bottom right (NB_cell, cell) partition is diagonal; it reflects cells modulated by cell drive actions acting on cell NBs. This is the CICD model for autocrine signaling, for example. The top left (NB_cytokine, cytokine) partition is null for patients. This says that cytokines cannot act as drive action sources for cytokine NBs, for example. The top right (NB_cytokine, cell) partition collects FIG. 19B patient specific bi-linear drive action detail. Values can be normalized counts for all bi-linear cell source drive actions that impact cytokine NBs. Columns identify those cells that are modulated by all cytokines. Across all patients, this partition shows considerable variability. Value counts are summations of all bi-linear cell drive actions of significance. They provide a measure for how often specific cells, modulated by any cytokine, are used to realize the modulated cell driven population change processes impacting cytokine NBs. Note that in FIG. 20: 1) Cell dominator NB rows in the bottom left partition show linear drive action stimulated by the column specified cytokines IP-10 and MCP-1. For patient MC1076-5a no other biomarkers contribute significantly. Other patients will have additional biomarker columns, as identified in FIGS. 19A-B. 2) The top right partition provides bi-linear drive action strengths for each column specified cell modulated by all cytokines acting on each row specified NB. Recall from FIG. 19B that of all cell modulators, biomarkers IP-10 & MCP-1 dominate. To support clinical treatment decision-making reverse engineering results need to be linked to the patient profiling measures that identify the test period environments associated with the cause & effect response realized and reverse engineered.

FIG. 20 depicts example patient MC1076-5a normalized drive action occurrence count matrix map for all sources acting on biomarker NBs. Partitions show: 1) Bottom left, linear drive action of column specified cytokine acting on cell NB's. 2) Bottom right, bi-linear (autocrine) drive action of column specified cell modulated by itself and acting on cell NB's. 3) Top left, null cytokines do not drive cytokine NBs. 4) Top right, bi-linear drive action of column specified cell (modulated by all cytokines) acting on cytokine NBs. Not shown: Across all patients considerable variability exists for both linear and bi-linear drive action information. When these cell and cytokine relationships are aggregated, patient action capacity profiling data emerges.

Figure 21:
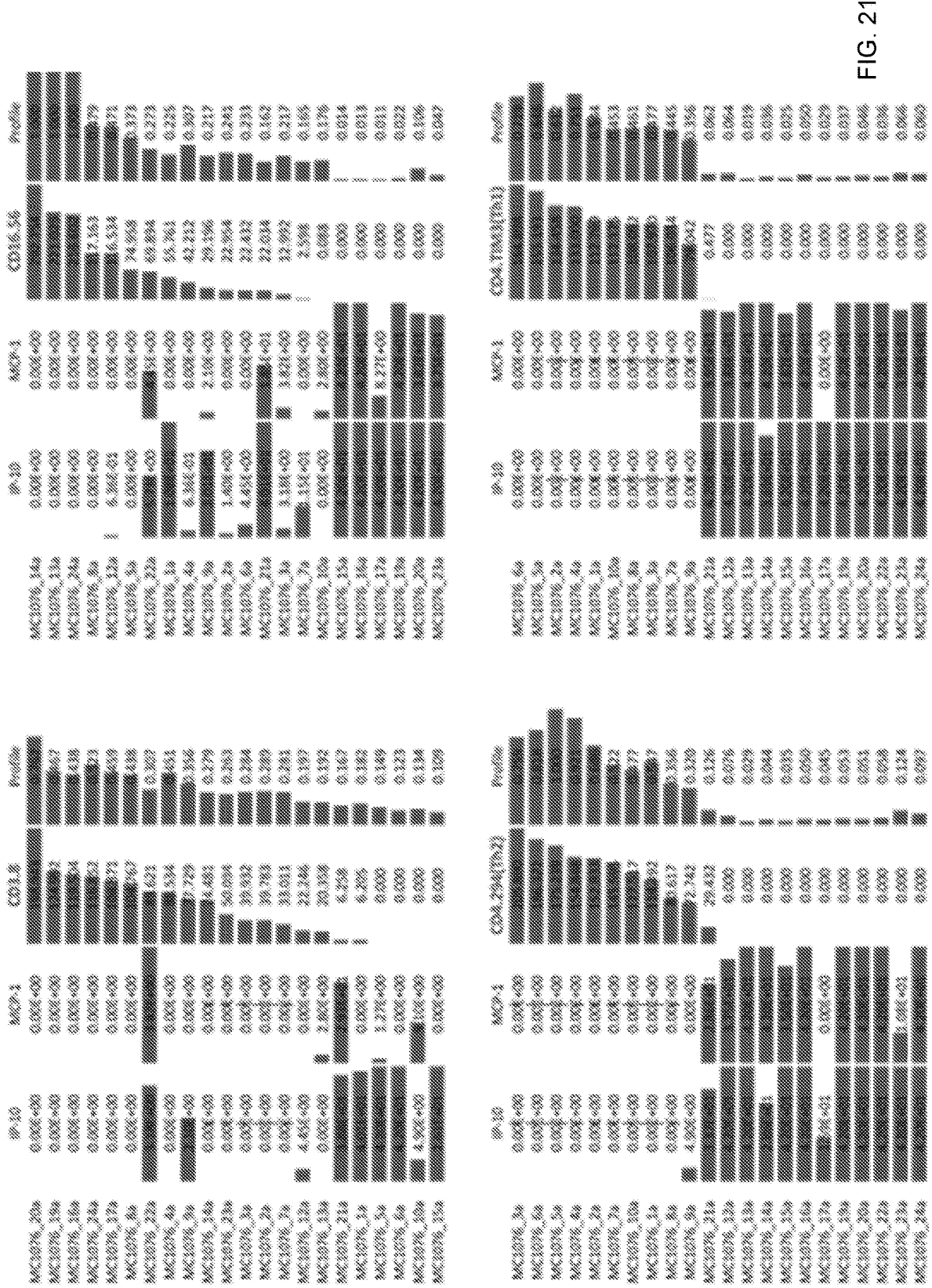
FIG. 21 depicts an example collection patient time record resultants and provides four sorted data tables.

Reverse Engineering: Drive Action Source Linked to Action Capacity Cell Profiling FIG. 19A depicts example quantification of the degree to which IP-10, MCP-1 and other relevant cytokines linearly drive all cell dominator NB's while FIG. 19B depicts example quantification of the degree to which IP-10, MCP-1 and other relevant cytokines modulate the bi-linear drive actions of cells acting on cytokine NB's. Both show that cytokines IP-10 and MCP-1 dominate the linear and bi-linear classes of biological drive action. FIG. 15 illustrates how patient test period profile measures are used to group and rank order patients with respect to cell & cytokine biomarker population class measures. FIG. 20 associated information from all CICD archived patient data shows that CICD reverse engineered information correlates with FIG. 15 patient test period profiling patient groups and rank ordering. The top partition of FIG. 20 provides relative strength values for each cell with IP-10 and MCP-1 dominating modulation generating a significant bi-linear drive action on cytokine dominator NBs. The lower left partition illustrates the domination role of IP-10 and MCP-1 as the source for linear drive actions impacting all cell dominated NB's while the lower right partition models significant autocrine signaling drive action FIG. 21 depicts an example collection patient time record resultants and provides four sorted data tables, one for each patient test period cell profiling measure shown in FIG. 15; namely CD3.8, CD16.56, CD4.294(Th2) and CD4.TIM3 (Th1). The intent is to show that CICD patient reverse engineering results correlate with patient profiling. In each table: Column 1 provides patient identification. Columns 2 and 3 are data aggregations computed per patient from the lower left FIG. 20 (NB_cell, cytokine) partition of each patient. These data columns respectively define the degree to which biomarkers IP-10, MCP-1 act as the linear chemotaxis recruitment and purging drive action sources for cell NBs. Column 4, for each patient identified row, is an aggregation of FIG. 20 patient (NB_cytokine, cell) partition column data for the column 4 header identified cell. It provides patient resultant bi-linear modulated cell source function drive action strength measures. Each table is sorted relative to this data column. Column 5 lists FIG. 15 patient test period cell profiling measures. Columns 4 and 5 together show a clear correlation between the reverse engineered strength measures of bi-linear modulated cell source resultant drive action per patient and patient test period cell profiling measures. Columns 2, 3 and 4, 5 together show a correlation between occurrences of IP-10 & MCP-1 being the dominating cytokines of linear drive action source vs. bi-linear drive action strength and patient test period cell profiling measures.

Together these tables support the hypothesis that IP-10 and MCP-1 are the dominant biomarkers for both linear and bi-linear source drive action. These model-based IP-10 & MCP-1 high behavioral response relevance predictions have now been independently validated for melanoma cancer patients. FIG. 21 shows that when cells have low raw biomarker population size values, the drive action is linear and the response is cellular recruitment or purging: otherwise the drive action is bi-linear and response is cellular creation of cells, cytokines and receptors. Although not evident in this table patient data also shows that a transition zone, rather than a sharp jump discontinuity, between linear and bi-linear drive action zones exists. Analysis of this transition zone is pending availability of cancer-free data. The most plausible explanation is that these CICD analysis observations are a reflection of a drive action characterization jump; i.e. a bifurcation predictable, from system initial conditions, as quantified by CICD's patient profile measures. This type of behavioral response is common and should be expected for non-linear problems of the predator-prey class that CICD analysis builds upon. Further work into clinical treatment pre-analysis characterization is awaiting cancer-free patient data processing and ability to create a full set of biomarker cancer sensitivity measures.

Conceptually, consider a collection of experiments done with a system of H2O molecules without environment measures for temperature and pressure. If the experiments are run in a random set of environments surrounding the triple point of water, it would be impossible understand the random occurrence of liquid, gas, solid results observed.

Results presented in FIGS. 20-21 strongly suggest that some pair of patient test period cell and cytokine profile measures, as used herein, will be foundational to understanding the complexity of cancer-free vs. cancer behavior relative patient behavior and that CICD provides the capability needed to probe complexity detail.

FIG. 21 depicts example cellular drive action source strength for all patients vs. patient cell test period resource availability characterization profile tables. Col 1 is Patient identification label, col 2 linear cellular drive action by IP-10 stimulation, col 3 linear cellular drive action by MCP-stimulation, col 4 bi-linear drive action of identified cell with IP-10 & MCP1 dominated modulation, col 5, normalized patient cell profile value. Results show: 1) There is a very high positive correlation between col 4 bi-linear cell drive strength and col 5 patient cell profile measures for patients and cells. 2) There is a very high inverse correlation between col 2 IP-10 & col 3 MCP-1 linear cell drive action strength and cell bi-linear drive action strength and patient cell profile measures for both patients and cells. 3) Correlations are reflective of a drive action bifurcation linked to cell profile measures. 4) For cancer patients cell profile measures identify bifurcation zones for cellular source drive action. 5) Cancer free patient results are pending data availability, the CICD pathway to these results will be identical that used for cancer patients.

Figure 22:
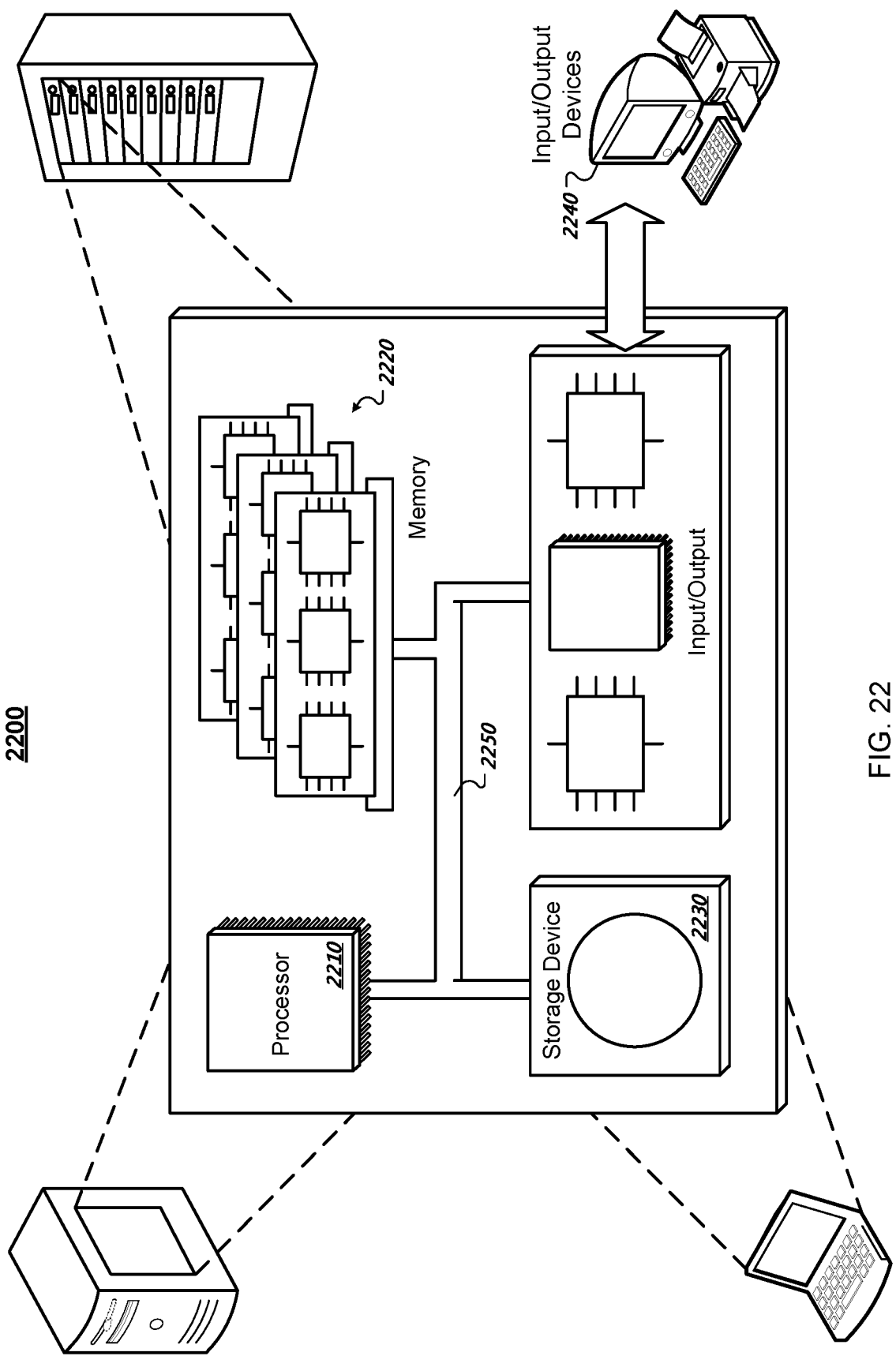
FIG. 22 illustrates a schematic diagram of an exemplary generic computer system.

FIG. 22 illustrates a schematic diagram of an exemplary generic computer system. The system 2200 can be used for the operations described above, such as those described in association the techniques 100 and 300, and/or in association with computer systems described above, such as the example CIDC computer system.

The system 2200 includes a processor 2210, a memory 2220, a storage device 2230, and an input/output device 2240. Each of the components 2210, 2220, 2230, and 2220 are interconnected using a system bus 2250. The processor 2210 is capable of processing instructions for execution within the system 2200. In one implementation, the processor 2210 is a single-threaded processor. In another implementation, the processor 2210 is a multi-threaded processor. The processor 2210 is capable of processing instructions stored in the memory 2220 or on the storage device 2230 to display graphical information for a user interface on the input/output device 2240.

The memory 2220 stores information within the system 2200. In one implementation, the memory 2220 is a computer-readable medium. In one implementation, the memory 2220 is a volatile memory unit. In another implementation, the memory 2220 is a non-volatile memory unit.

The storage device 2230 is capable of providing mass storage for the system 2200. In one implementation, the storage device 2230 is a computer-readable medium. In various different implementations, the storage device 2230 may be a floppy disk device, a hard disk device, an optical disk device, or a tape device.

The input/output device 2240 provides input/output operations for the system 2200. In one implementation, the input/output device 2240 includes a keyboard and/or pointing device. In another implementation, the input/output device 2240 includes a display unit for displaying graphical user interfaces.

Embodiments of the subject matter, the functional operations and the processes described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A computer-implemented method comprising:
   accessing, by a computer system, patient-derived blood data;
   identifying, by the computer system, biomarker pair interactions based on signal processing of the patient-derived blood data;

generating, by the computer system, a data model that characterizes one or more aspects of human immune system interactions based on reverse engineering of the human immune system interactions using the identified biomarker pair interactions;

evaluating, by the computer system, suitability of the data model to be used in treatment-based decision making, wherein the evaluating comprises:

statistically testing, by the computer system, the accuracy of the data model in characterizing correlations between biomarker pairs;

decomposing, by the computer system, the data model to determine (i) model order accuracy, (ii) whether biomarker nodes act together or opposite each other, and (iii) normalized data with dynamic effects of homeostasis removed, wherein decomposing the data model comprises using a function to model growth or decay of observed biomarkers, wherein the function includes (i) linear terms that model the linear growth or decay of the observed biomarkers responding to the actions of unspecified cells and (ii) multi-linear terms that model the non-linear growth or decay of the observed biomarkers responding to specified cellular action triggered by specified biomarkers; and quantifying, by the computer system, degrees to which the data model accurately correlates patient treatments to patient outcomes using one or more sets of known patient treatments and outcomes; and providing, by the computer system, the data model for use in treatment-based decision making based on the evaluating.

2. The computer-implemented method of claim 1, wherein the data model comprises a Kolmogorov-Gabor polynomial knowledge constraint model.

3. The computer-implemented method of claim 1, wherein the data model is generated using one or more predator-prey equations.

4. The computer-implemented method of claim 3, wherein the data model is generated further using one or more reverse engineering techniques that cause the data model to correlate natural modes of system behavior.

5. The computer-implemented method of claim 1, wherein the data model is generated to model biomarker cause and effect dynamic integration networks.

6. A computer system comprising:
a data storage device storing patient-derived blood data;
one or more computing devices that each include one or more processors and memory storing instructions, wherein the instructions, when executed, cause the one or more processors to perform operations comprising:
accessing the patient-derived blood data from the data storage device;
identifying biomarker pair interactions based on signal processing of the patient-derived blood data;
generating a data model that characterizes one or more aspects of human immune system interactions based on reverse engineering of the human immune system interactions using the identified biomarker pair interactions;
evaluating suitability of the data model to be used in treatment-based decision making, wherein the evaluating comprises:
statistically testing the accuracy of the data model in characterizing correlations between biomarker pairs;
decomposing the data model to determine (i) model order accuracy, (ii) whether biomarker nodes act together or opposite each other, and (iii) normalized data with dynamic effects of homeostasis removed, wherein decomposing the data model comprises using a function to model growth or decay of observed biomarkers, wherein the function includes (i) linear terms that model the linear growth or decay of the observed biomarkers responding to the actions of unspecified cells and (ii) multi-linear terms that model the non-linear growth or decay of the observed biomarkers responding to specified cellular action triggered by specified biomarkers; and
quantifying degrees to which the data model accurately correlates patient treatments to patient outcomes using one or more sets of known patient treatments and outcomes; and
providing the data model for use in treatment-based decision making based on the evaluating.

7. The system of claim 6, wherein the data model comprises a Kolmogorov-Gabor polynomial knowledge constraint model.

8. The system of claim 6, wherein the data model is generated using one or more predator-prey equations.

9. The system of claim 8, wherein the data model is generated further using one or more reverse engineering techniques that cause the data model to correlate natural modes of system behavior.

10. The system of claim 6, wherein the data model is generated to model biomarker cause and effect dynamic integration networks.

11. A non-transitory computer readable medium storing instructions that, when executed by one or more computing devices, cause the one or more computing devices to perform operations comprising:
accessing patient-derived blood data;
identifying biomarker pair interactions based on signal processing of the patient-derived blood data;
generating a data model that characterizes one or more aspects of human immune system interactions based on reverse engineering of the human immune system interactions using the identified biomarker pair interactions;
evaluating suitability of the data model to be used in treatment-based decision making, wherein the evaluating comprises:
statistically testing the accuracy of the data model in characterizing correlations between biomarker pairs;
decomposing the data model to determine (i) model order accuracy, (ii) whether biomarker nodes act together or opposite each other, and (iii) normalized data with dynamic effects of homeostasis removed, wherein decomposing the data model comprises using a function to model growth or decay of observed biomarkers, wherein the function includes (i) linear terms that model the linear growth or decay of the observed biomarkers responding to the actions of unspecified cells and (ii) multi-linear terms that model the non-linear growth or decay of the observed biomarkers responding to specified cellular action triggered by specified biomarkers; and
quantifying degrees to which the data model accurately correlates patient treatments to patient outcomes using one or more sets of known patient treatments and outcomes; and providing the data model for use in treatment-based decision making based on the evaluating.

12. The non-transitory medium of claim 11, wherein the data model comprises a Kolmogorov-Gabor polynomial knowledge constraint model.

13. The non-transitory medium of claim 11, wherein the data model is generated using one or more predator-prey equations.

14. The non-transitory medium of claim 13, wherein the data model is generated further using one or more reverse engineering techniques that cause the data model to correlate natural modes of system behavior.

15. The non-transitory medium of claim 11, wherein the data model is generated to model biomarker cause and effect dynamic integration networks.

* * * * *